United States Patent
Baxter et al.

(10) Patent No.: US 8,267,932 B2
(45) Date of Patent: *Sep. 18, 2012

(54) DEFLECTABLE SHEATH CATHETERS

(75) Inventors: Lincoln S. Baxter, Centerville, MA (US); Jeffrey M. Arnold, Wellesley, MA (US); Gerald Melsky, Lexington, MA (US)

(73) Assignee: CardioFocus, Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,105

(22) Filed: May 2, 2011

(65) Prior Publication Data

US 2011/0245828 A1 Oct. 6, 2011

Related U.S. Application Data

(60) Division of application No. 11/062,905, filed on Feb. 22, 2005, now Pat. No. 7,935,108, which is a continuation-in-part of application No. 10/357,156, filed on Feb. 3, 2003, now Pat. No. 8,025,661, which is a continuation-in-part of application No. 09/924,393, filed on Aug. 7, 2001, now Pat. No. 6,676,656, said application No. 11/062,905 is a continuation-in-part of application No. 10/674,114, filed on Sep. 29, 2003, now Pat. No. 6,942,657, which is a continuation of application No. 09/616,275, filed on Jul. 14, 2000, now Pat. No. 6,626,900, which is a continuation-in-part of application No. 09/602,420, filed on Jun. 23, 2000, now Pat. No. 6,572,609, which is a continuation-in-part of application No. 09/357,355, filed on Jul. 14, 1999, now Pat. No. 6,423,055, said application No. 11/062,905 is a continuation-in-part of application No. 10/865,558, filed on Jun. 10, 2004.

(60) Provisional application No. 60/477,374, filed on Jun. 10, 2003.

(51) Int. Cl.
*A61B 18/18* (2006.01)

(52) U.S. Cl. ............... 606/41; 606/45; 606/49; 607/101; 607/119

(58) Field of Classification Search .................... 606/34, 606/37, 40, 41, 45, 47–50; 607/96, 101, 607/102, 116, 119, 122

See application file for complete search history.

(56) References Cited

U.S. PATENT DOCUMENTS 3,417,745 A 12/1968 Sheldon
(Continued)

FOREIGN PATENT DOCUMENTS

DE 94117543 11/1994
(Continued)

OTHER PUBLICATIONS

Bredikis, J. et al. "Laser Destruction of the Atrioventricular Bundle Using the Cardiac Endoscope" Kardiologiia, 1988, 28(8): 94-96.

(Continued)

*Primary Examiner* — Ahmed Farah
(74) *Attorney, Agent, or Firm* — Leason Ellis LLP

(57) ABSTRACT

The present invention provides devices and methods for the treatment of atrial fibrillation. In one embodiment a deflectable sheath catheter includes an elongate catheter body having proximal and distal ends, the distal end having a distal tip region that includes a plurality of flexible segments with varying degrees of stiffness. A handle portion can be located at the proximal end of the catheter body to provide a steering mechanism that causes the distal tip region to deflect according to a compound curve.

25 Claims, 28 Drawing Sheets

U.S. PATENT DOCUMENTS

| | | |
|---|---|---|
| 3,821,510 A | 6/1974 | Muncheryan |
| 4,224,929 A | 9/1980 | Furihata et al. |
| 4,233,493 A | 11/1980 | Nath et al. |
| 4,273,109 A | 6/1981 | Enderby |
| 4,336,809 A | 6/1982 | Clark |
| 4,445,892 A | 5/1984 | Hussein et al. |
| 4,585,298 A | 4/1986 | Mori et al. |
| 4,625,724 A | 12/1986 | Shibamoto Hiroshi et al. |
| 4,660,925 A | 4/1987 | McCaughan, Jr. |
| 4,701,166 A | 10/1987 | Groshong et al. |
| 4,718,417 A | 1/1988 | Kittrell et al. |
| 4,770,653 A | 9/1988 | Shturman |
| 4,781,681 A | 11/1988 | Sharrow et al. |
| 4,819,632 A | 4/1989 | Davies et al. |
| 4,842,390 A | 6/1989 | Sottini et al. |
| 4,852,567 A | 8/1989 | Sinofsky |
| 4,860,743 A | 8/1989 | Abela |
| 4,862,886 A | 9/1989 | Clarke et al. |
| 4,878,492 A | 11/1989 | Sinofsky et al. |
| 4,878,725 A | 11/1989 | Hessel |
| 4,913,142 A | 4/1990 | Kittrell et al. |
| 4,961,738 A | 10/1990 | Mackin |
| 5,026,367 A | 6/1991 | Leckrone et al. |
| 5,030,201 A | 7/1991 | Palestrant |
| 5,053,033 A | 10/1991 | Clarke |
| 5,071,417 A | 12/1991 | Sinofsky |
| 5,078,681 A | 1/1992 | Kawashima et al. |
| 5,090,959 A | 2/1992 | Samson et al. |
| 5,109,859 A | 5/1992 | Jenkins |
| 5,125,925 A | 6/1992 | Lundahl |
| 5,133,709 A | 7/1992 | Prince |
| 5,140,987 A | 8/1992 | Schuger et al. |
| 5,151,096 A | 9/1992 | Khoury |
| 5,151,097 A | 9/1992 | Daikuzono et al. |
| 5,163,935 A | 11/1992 | Black et al. |
| 5,169,395 A | 12/1992 | Narciso, Jr. |
| 5,188,632 A | 2/1993 | Goldenberg |
| 5,188,634 A | 2/1993 | Hussein et al. |
| 5,190,538 A | 3/1993 | Hussein et al. |
| 5,196,005 A | 3/1993 | Doiron et al. |
| 5,207,699 A | 5/1993 | Coe |
| 5,209,748 A | 5/1993 | Daikuzono et al. |
| 5,219,346 A | 6/1993 | Wagnieres et al. |
| 5,242,438 A | 9/1993 | Saadakmanesh et al. |
| 5,261,904 A | 11/1993 | Baker et al. |
| 5,269,777 A | 12/1993 | Doiron et al. |
| RE34,544 E | 2/1994 | Spears |
| 5,318,024 A | 6/1994 | Kittrell et al. |
| 5,330,465 A | 7/1994 | Doiron et al. |
| 5,337,381 A | 8/1994 | Biswas et al. |
| 5,350,375 A | 9/1994 | Deckelbaum et al. |
| 5,363,458 A | 11/1994 | Pan et al. |
| 5,368,564 A | 11/1994 | Savage |
| 5,374,953 A | 12/1994 | Sasaki et al. |
| 5,380,316 A | 1/1995 | Aita et al. |
| 5,380,317 A | 1/1995 | Everett et al. |
| 5,395,362 A | 3/1995 | Sacharoff et al. |
| 5,401,270 A | 3/1995 | Muller et al. |
| 5,409,483 A | 4/1995 | Campbell et al. |
| 5,417,653 A | 5/1995 | Sahota et al. |
| 5,418,649 A | 5/1995 | Igarashi et al. |
| 5,423,805 A | 6/1995 | Brucker et al. |
| 5,427,119 A | 6/1995 | Swartz et al. |
| 5,431,647 A | 7/1995 | Purcell, Jr. et al. |
| 5,437,660 A | 8/1995 | Johnson et al. |
| 5,441,497 A | 8/1995 | Narciso, Jr. |
| 5,445,608 A | 8/1995 | Chen et al. |
| 5,464,404 A | 11/1995 | Abela et al. |
| 5,482,037 A | 1/1996 | Borghi et al. |
| 5,496,305 A | 3/1996 | Kittrell et al. |
| 5,497,774 A | 3/1996 | Swartz et al. |
| 5,507,725 A | 4/1996 | Savage et al. |
| 5,531,664 A | 7/1996 | Adachi et al. |
| 5,536,265 A | 7/1996 | Van den Bergh et al. |
| 5,575,766 A | 11/1996 | Swartz et al. |
| 5,605,162 A | 2/1997 | Mirzaee et al. |
| 5,613,965 A | 3/1997 | Muller |
| 5,643,253 A | 7/1997 | Baxter et al. |
| 5,649,923 A | 7/1997 | Gregory et al. |
| 5,662,712 A | 9/1997 | Pathak et al. |
| 5,680,860 A | 10/1997 | Imran |
| 5,690,611 A | 11/1997 | Swartz et al. |
| 5,693,043 A | 12/1997 | Kittrell et al. |
| 5,700,243 A | 12/1997 | Narciso, Jr. |
| 5,702,438 A | 12/1997 | Avitall |
| 5,722,401 A | 3/1998 | Pietroski et al. |
| 5,725,522 A | 3/1998 | Sinofsky |
| 5,759,619 A | 6/1998 | Jin et al. |
| 5,769,843 A | 6/1998 | Abela et al. |
| 5,772,590 A | 6/1998 | Webster, Jr. |
| 5,773,835 A | 6/1998 | Sinofsky |
| 5,779,646 A | 7/1998 | Koblish et al. |
| 5,782,239 A | 7/1998 | Webster, Jr. |
| 5,782,899 A | 7/1998 | Imran |
| 5,800,482 A | 9/1998 | Pomeranz et al. |
| 5,807,395 A | 9/1998 | Mulier et al. |
| 5,823,955 A | 10/1998 | Kuck et al. |
| 5,824,005 A | 10/1998 | Motamedi et al. |
| 5,830,209 A | 11/1998 | Savage et al. |
| 5,833,682 A | 11/1998 | Amplatz et al. |
| 5,843,073 A | 12/1998 | Sinofsky |
| 5,845,646 A | 12/1998 | Lemelson |
| 5,860,974 A | 1/1999 | Abele |
| 5,885,278 A | 3/1999 | Fleischman |
| 5,891,133 A | 4/1999 | Murphy-Chutorian |
| 5,891,134 A | 4/1999 | Goble et al. |
| 5,904,651 A | 5/1999 | Swanson et al. |
| 5,908,415 A | 6/1999 | Sinofsky |
| 5,931,834 A | 8/1999 | Murphy-Chutorian et al. |
| 5,938,660 A | 8/1999 | Swartz et al. |
| 5,947,959 A | 9/1999 | Sinofsky |
| 5,967,984 A | 10/1999 | Chu et al. |
| 5,971,983 A | 10/1999 | Lesh |
| 5,995,875 A | 11/1999 | Blewett et al. |
| 6,004,269 A | 12/1999 | Crowley et al. |
| 6,012,457 A | 1/2000 | Lesh |
| 6,024,740 A | 2/2000 | Lesh et al. |
| 6,056,744 A | 5/2000 | Edwards |
| 6,064,902 A | 5/2000 | Haissaguerre et al. |
| 6,071,279 A | 6/2000 | Whayne et al. |
| 6,071,281 A | 6/2000 | Burnside et al. |
| 6,071,282 A | 6/2000 | Fleischman |
| 6,071,302 A | 6/2000 | Sinofsky et al. |
| 6,086,581 A | 7/2000 | Reynolds et al. |
| 6,090,084 A | 7/2000 | Hassett et al. |
| 6,099,514 A | 8/2000 | Sharkey et al. |
| 6,102,905 A | 8/2000 | Baxter et al. |
| 6,117,071 A | 9/2000 | Ito et al. |
| 6,117,101 A | 9/2000 | Diederich et al. |
| 6,120,496 A | 9/2000 | Whayne et al. |
| 6,146,379 A | 11/2000 | Fleischman et al. |
| 6,159,203 A | 12/2000 | Sinofsky |
| 6,161,543 A | 12/2000 | Cox et al. |
| 6,164,283 A | 12/2000 | Lesh |
| 6,179,835 B1 | 1/2001 | Panescu et al. |
| 6,214,002 B1 | 4/2001 | Fleischman et al. |
| 6,217,510 B1 | 4/2001 | Ozawa et al. |
| 6,235,025 B1 | 5/2001 | Swartz et al. |
| 6,237,605 B1 | 5/2001 | Vaska et al. |
| 6,240,231 B1 | 5/2001 | Ferrera et al. |
| 6,245,064 B1 | 6/2001 | Lesh et al. |
| 6,251,092 B1 | 6/2001 | Qin et al. |
| 6,251,109 B1 | 6/2001 | Hassett et al. |
| 6,254,599 B1 | 7/2001 | Lesh et al. |
| 6,270,492 B1 | 8/2001 | Sinofsky |
| 6,305,378 B1 | 10/2001 | Lesh |
| 6,312,427 B1 | 11/2001 | Berube et al. |
| 6,314,962 B1 | 11/2001 | Vaska et al. |
| 6,325,797 B1 | 12/2001 | Stewart et al. |
| 6,352,531 B1 | 3/2002 | O'Connor et al. |
| 6,383,151 B1 | 5/2002 | Diederich et al. |
| 6,394,949 B1 | 5/2002 | Crowley et al. |
| 6,416,511 B1 | 7/2002 | Lesh |
| 6,423,055 B1 | 7/2002 | Farr et al. |
| 6,423,058 B1 | 7/2002 | Edwards et al. |
| 6,471,697 B1 | 10/2002 | Lesh |
| 6,485,485 B1 | 11/2002 | Winston et al. |

| | | |
|---|---|---|
| 6,500,174 B1 | 12/2002 | Maguire et al. |
| 6,502,576 B1 | 1/2003 | Lesh |
| 6,503,247 B2 | 1/2003 | Swartz et al. |
| 6,514,249 B1 | 2/2003 | Maguire et al. |
| 6,522,933 B2 | 2/2003 | Nguyen |
| 6,544,262 B2 | 4/2003 | Fleischman |
| 6,547,780 B1 | 4/2003 | Sinofsky |
| 6,554,794 B1 | 4/2003 | Mueller et al. |
| 6,558,375 B1 | 5/2003 | Sinofsky et al. |
| 6,562,020 B1 | 5/2003 | Constantz et al. |
| 6,572,609 B1 | 6/2003 | Farr et al. |
| 6,579,278 B1 | 6/2003 | Bencini |
| 6,579,285 B2 | 6/2003 | Sinofsky |
| 6,582,536 B2 | 6/2003 | Shimada |
| 6,605,055 B1 | 8/2003 | Sinofsky |
| 6,605,084 B2 | 8/2003 | Acker et al. |
| 6,626,900 B1 | 9/2003 | Sinofsky et al. |
| 6,635,054 B2 | 10/2003 | Fjield et al. |
| 6,648,875 B2 | 11/2003 | Simpson et al. |
| 6,669,655 B1 | 12/2003 | Acker et al. |
| 6,676,656 B2 | 1/2004 | Sinofsky |
| 6,679,873 B2 | 1/2004 | Rabiner et al. |
| 6,702,780 B1 | 3/2004 | Gilboa et al. |
| 6,771,996 B2 | 8/2004 | Bowe et al. |
| 6,896,673 B2 | 5/2005 | Hooven |
| 6,907,298 B2 | 6/2005 | Smits et al. |
| 6,916,306 B1 | 7/2005 | Jenkins et al. |
| 6,932,809 B2 | 8/2005 | Sinofsky |
| 6,942,657 B2 | 9/2005 | Sinofsky et al. |
| 6,953,457 B2 | 10/2005 | Farr et al. |
| 6,997,924 B2 | 2/2006 | Schwartz et al. |
| 7,207,984 B2 | 4/2007 | Farr et al. |
| 7,357,796 B2 | 4/2008 | Farr et al. |
| 7,935,108 B2 * | 5/2011 | Baxter et al. ............ 606/15 |
| 8,025,661 B2 | 9/2011 | Arnold et al. |
| 2001/0030107 A1 | 10/2001 | Simpson |
| 2002/0019627 A1 | 2/2002 | Maguire et al. |
| 2002/0029062 A1 | 3/2002 | Satake |
| 2002/0065512 A1 | 5/2002 | Fjield et al. |
| 2002/0091383 A1 | 7/2002 | Hooven |
| 2002/0115995 A1 | 8/2002 | Lesh et al. |
| 2002/0120264 A1 | 8/2002 | Crowley et al. |
| 2002/0183729 A1 | 12/2002 | Farr et al. |
| 2002/0183739 A1 | 12/2002 | Long |
| 2003/0050632 A1 | 3/2003 | Fjield et al. |
| 2003/0065307 A1 | 4/2003 | Lesh |
| 2003/0069620 A1 | 4/2003 | Li |
| 2003/0111085 A1 | 6/2003 | Lesh |
| 2003/0120270 A1 | 6/2003 | Acker |
| 2003/0144657 A1 | 7/2003 | Bowe et al. |
| 2003/0158550 A1 | 8/2003 | Ganz et al. |
| 2003/0171746 A1 | 9/2003 | Fleischman |
| 2004/0006333 A1 | 1/2004 | Arnold et al. |
| 2004/0054360 A1 | 3/2004 | Schwartz et al. |
| 2004/0059397 A1 | 3/2004 | Sinofsky et al. |
| 2004/0122290 A1 | 6/2004 | Irion et al. |
| 2005/0038419 A9 | 2/2005 | Arnold et al. |
| 2005/0065504 A1 | 3/2005 | Melsky et al. |
| 2005/0288654 A1 | 12/2005 | Nieman et al. |
| 2006/0253113 A1 | 11/2006 | Arnold et al. |
| 2007/0078451 A1 | 4/2007 | Arnold et al. |
| 2008/0039746 A1 | 2/2008 | Hissong et al. |
| 2008/0108870 A1 | 5/2008 | Wiita et al. |
| 2008/0195088 A1 | 8/2008 | Farr et al. |
| 2009/0221996 A1 | 9/2009 | Lesh et al. |
| 2009/0221997 A1 | 9/2009 | Arnold et al. |
| 2009/0275934 A1 | 11/2009 | Baxter et al. |
| 2009/0299354 A1 | 12/2009 | Melsky et al. |
| 2009/0326320 A1 | 12/2009 | Sinofsky et al. |
| 2011/0082449 A1 | 4/2011 | Melsky et al. |
| 2011/0082450 A1 | 4/2011 | Melsky et al. |
| 2011/0082451 A1 | 4/2011 | Melsky |
| 2011/0082452 A1 | 4/2011 | Melsky et al. |
| 2011/0245822 A1 | 10/2011 | Baxter et al. |
| 2011/0245828 A1 | 10/2011 | Baxter et al. |

FOREIGN PATENT DOCUMENTS

| | | |
|---|---|---|
| EP | 0214712 | 3/1987 |
| EP | 0292621 | 11/1988 |
| EP | 0292695 | 11/1988 |
| EP | 0299448 | 1/1989 |
| EP | 0311458 | 4/1989 |
| EP | 0437181 | 7/1991 |
| EP | 0437183 | 7/1991 |
| EP | 0439629 | 8/1991 |
| EP | 0598984 | 6/1994 |
| EP | 0792664 | 9/1997 |
| EP | 1072231 | 1/2001 |
| EP | 1331893 | 12/2004 |
| FR | 2798371 A | 3/2001 |
| JP | 2003-210028 A | 7/2003 |
| JP | 2004-065076 A | 3/2004 |
| WO | WO 9217243 | 10/1992 |
| WO | WO 9306888 | 4/1993 |
| WO | WO 9219680 | 10/1993 |
| WO | WO 9319680 | 10/1993 |
| WO | WO 9325155 | 12/1993 |
| WO | WO 9417434 | 8/1994 |
| WO | WO 9426184 | 11/1994 |
| WO | WO 9607451 | 3/1996 |
| WO | WO 9634646 | 11/1996 |
| WO | WO 9640342 | 12/1996 |
| WO | WO 9737714 | 10/1997 |
| WO | WO 00/67832 | 11/2000 |
| WO | WO 01/03599 A2 | 1/2001 |
| WO | WO 0113812 | 3/2001 |
| WO | WO 01/64123 | 9/2001 |
| WO | WO 02/096479 | 12/2002 |
| WO | WO 03090835 | 11/2003 |
| WO | WO 2004-110258 | 12/2004 |

OTHER PUBLICATIONS

Chevalier, P. et al. "Thoracoscopic Epicardial Radiofrequency Ablation for Vagal Atrial Fibrillation in Dogs" PACE, 1999, 22: 880-886.

Froelich, J. et al. "Evaluation of a Prototype Steerable Angioscopic Laser Catheter in a Canine Model: A Feasibility Study" Cardiovasc Intervent Radiol, 1993 16: 235-238.

Fujimura, O. et al. "Direct in Vivo Visualization of Right Cardiac Anatomy by Fiberoptic Endoscopy" Angiology; 1995, 46(3): 201-208.

Gamble, W. and Innis, R. "Experimental Intracardiac Visualization" NEJM, 1967, 276(25): 1397-1403.

Hirao, K. et al. "Transcatheter Neodymium-Yttrium-Aluminum Garnet Laser Coagulation of Canine Ventricle Using a Balloon-Tipped Cardioscope" Jpn Circ. J. 1997, 61: 695-703.

Kean, D. et al. "Pulmonary Vein Isolation for Atrial Fibrillation" Rev Cardiovasc Med., 2002, 3(4): 167-175.

Kuo, C. et al. "In Vivo Angioscopic Visualization of Right Heart Structure in Dogs by Means of Balloon-Tipped Fiberoptic Endoscope: Potential Role in Percutaneous Ablative Procedures." American Heart J., 1994, 127: 187-197.

Nakagawa, H. et al. "Cardioscopic Catheter Ablation with Non-contact, Pulsed Nd: YAG Laser Using Saline Inflated Balloon Catheter," Presentation JACC 1998; 31:118A-119A.

Obelienius, V. et al. "Transvenous Ablation of the Atrioventricular Conduction System by Laser Irradiation Under Endoscopic Control" Lasers in Surgery Medicine, 1985, 5: 469-474.

Roggan, A. et al. "Optical Properties of Circulating Human Blood in the Wavelength Range 400-2400nm" J. Biomedical Optics, 1999, 4(1): 36-46.

Saliba, W. et al. "Cicumferential Ultrasound Ablation for Pulmonary Vein Isolation: Analysis of Acute and Chronic Failures" J. Cardiovascular Electrophysiology, 2002, 13(10): 957-961.

Shure, D. et al. "Identification of Pulmonary Emboli in the Dog: Comparison of Angioscopy and Perfusion Scanning" Circulation, 1981, 64(3): 618-621.

Shure, D. et al. "Fiberoptic Angioscopy: Role in the Diagnosis of Chronic Pulmonary Arterial Obstruction" Ann Int Med., 1985, 103: 844-850.

Tanabe, T et al. "Cardiovascular Fiberoptic Endoscopy: Development and Clinical Application" Surgery, 1980, 87(4): 375-379.

Uchida, Y. et al. "Fiberoptic Angioscopy of Cardiac Chambers, Valves, and Great Vessels Using a Guiding Balloon Catheter in Dogs." American Heart J., 1998, 115(6): 1297-1302.

Uchida, Y. et al. "Percutaneous Pulmonary Angioscopy Using a Guiding Balloon Catheter" Clin. Cardiol., 1988, 11:143-148.

Vanermen, H. et al. "Minimally Invasive Video-Assisted Mitral Valve Surgery: From Port-Access Towards a Totally Endoscopic Procedure" J. Card Surg., 2000, 15: 51-60.

Yamamoto, N. et al. "Nonfluoroscopic Guidance for Catheter Placement into the Coronary Sinus under Direct Vision Using a Balloon-Tipped Cardioscope" PACE, 1998; 21: 1724-1729.

Fujimura, O. et al. "Direct In Vivo Visualization of Right Cardiac Anatomy by Fiberoptic Endoscopy: Observation of Radiofrequency-Induced Acute Lesions Around the Ostium of the Coronary Sinus" European Heart J., 1994, 15: 534-540.

Tanaka, K. et al., "Endoscopy-Assisted Radiofrequency Ablation Around the Coronary Sinus Ostium in Dogs: Its Effects on Atrioventricular Nodal Properties and Ventricular Response During Atrial Fibrillation," Journal of Cardiovascular Electrophysiology, vol. 7, No. 11, Nov. 1996, pp. 1063-1073.

* cited by examiner

DEFLECTABLE SHEATH CATHETERS

The pending application is a divisional of U.S. patent application Ser. No. 11/062,905, filed Feb. 22, 2005, which is a continuation-in-part of U.S. patent application Ser. No. 10/357,156, filed Feb. 3, 2003, which is a continuation-in-part of U.S. patent application Ser. No. 09/924,393, filed Aug. 7, 2001, now U.S. Pat. No. 6,676,656 (issued Jan. 13, 2004).

U.S. patent application Ser. No. 11/062,905, filed Feb. 22, 2005, of which the pending application is a divisional, is also a continuation-in-part of U.S. patent application Ser. No. 10/674,114, filed Sep. 29, 2003 now U.S. Pat. No. 6,942,657 (issued Sep. 13, 2005), which is a continuation of U.S. patent application Ser. No. 09/616,275, filed Jul. 14, 2000, now U.S. Pat. No. 6,626,900 (issued Sep. 30, 2003), which is a continuation-in-part of U.S. patent application Ser. No. 09/602,420, filed Jun. 23, 2000, now U.S. Pat. No. 6,572,609 (issued Jun. 3, 2003), which is a continuation-in-part of U.S. patent application Ser. No. 09/357,355, filed Jul. 14, 1999, now U.S. Pat. No. 6,423,055 (issued Jul. 22, 2002).

U.S. patent application Ser. No. 11/062,905, filed Feb. 22, 2005, of which the pending application is a divisional, is also a continuation-in-part of U.S. patent application Ser. No. 10/865,558, filed Jun. 10, 2004, which claims priority to U.S. Provisional Application Ser. No. 60/477,374, filed Jun. 10, 2003.

FIELD OF THE INVENTION

The present invention generally relates to methods and devices for treating atrial fibrillation, and in particular to deflectable guide catheters which are used to provide access and delivery of ablation instruments, medications, or fluids into the heart.

BACKGROUND OF THE INVENTION

Cardiac arrhythmias, such as atrial fibrillation, are irregularities in the normal beating pattern of the heart and can originate in either the atria or the ventricles. Atrial fibrillation is characterized by rapid randomized contractions of the atrial myocardium, causing an irregular, often-rapid ventricular rate, and can give rise to other forms of cardiovascular disease, including congestive heart failure, rheumatic heart disease, coronary artery disease, left ventricular hypertrophy, cardiomyopathy or hypertension.

Treatments for atrial fibrillation have focused on the pulmonary veins, which have been identified as one of the origins of errant electrical signals responsible for activating atrial fibrillation. In one known approach, tissue is ablated in a circumferential pattern at locations such as the within the pulmonary veins, at the ostia of the pulmonary veins, or surrounding the pulmonary veins. By ablating the heart tissue at these locations, the electrical conductivity from one segment to another can be blocked such that the resulting segments become too small to sustain the fibrillatory process on their own.

In order to reach locations within or surrounding the heart, guide catheters are commonly used. Most guide catheters have proximal and distal ends connected by a long, tubular body having one or more lumens formed therein. The proximal end of the catheter usually includes a handle for control of the catheter by the operator and various ports for introduction of fluids and instruments through the catheter lumen, and the distal end includes a tip which is inserted into the patient. For example, in vascular applications, the tip of the catheter can be inserted into a major vein, artery, or other body cavity. The catheter is then further inserted and guided to the area of concern. Moreover, the catheter can also function as a "sheath" or "guide catheter" in that it can be used a delivery conduit for other tools, such as balloons and/or stents for performing angioplasty or other instruments mapping electrodes and ablation devices for conducting procedures within the heart.

Current methods for inserting and guiding a catheter include the use of a guide wire where the guide wire is fed into position within the patient and then the catheter is passed over the guide wire. However, one drawback associated with this method, when the target ablation sites are in or near the pulmonary veins on the posterior surface of the heart, is that it is often difficult, if not impossible, to advance the guide wire all the way to the ultimate target site due to the shape of the heart muscle.

Alternatively, a steerable catheter can be used. Steerable catheters require an ability to selectively deflect the distal tip of the catheter in a desired direction by permitting an operator to adjust the direction of advancement of the distal end of the catheter, as well as to position the distal portion of the catheter. The deflection of the distal tip is typically provided by one or more pull wires that are attached at the distal end of the catheter and extend to a control handle such that the surgeon can selectively deflect the tip and/or rotate the catheter shaft to navigate into the correct position.

When designing such steerable catheters for access into the heart, it is important to have sufficient flexibility in the catheter shaft so that when the catheter is advanced through a blood vessel or heart chamber it can follow the inherent curvature of the biological structures without puncturing them. However, achieving a balance between the "pushability" of the catheter (that is, the ability to direct the tip of the catheter to the target location without buckling or kinking) and the necessary stiffness to allow the catheter to access the heart, especially when navigating the sharp turns necessary to access locations in the left atrium of the heart, can be difficult.

Prior art deflectable catheters typically have a single stiffness value, or at best, one stiffness value for the catheter body and one stiffness value for the deflectable tip. As a result, these catheters often require large spatial volumes in which to bend and are unable to make tight turns that are sometimes necessary to reach a target region without causing trauma to a patient. Particularly, access to the left atrium for the treatment of atrial fibrillation is particularly difficult when the ultimate target region is in the vicinity of the right inferior pulmonary vein, as this vein is usually the closest to the transseptal puncture, requiring the catheter to turn 180° in direction in order to achieve proper orientation.

Currently methods to address this issue include using a set of sheath catheters with different curves and removing one catheter and replacing it with another, several times. However, this exchange is time consuming and can present additional risks, such as accidental entrainment of air embolisms.

More difficulties arise when the catheter includes an ablation instrument having a balloon, as additional maneuvering can be required to properly orient the balloon within or at the mouth of the vein. Further, axial force may be required in order to occlude the pulmonary vein at the ostium and the lack of stiffness of most catheters renders the application of sufficient force to successfully seal the vein prior to ablation problematic.

Accordingly, there exists a need for deflectable sheath catheters that can navigate and access narrow and limited spaces leading into, and within the heart, especially the left atrium. There also exists a need for improved methods of treating atrial fibrillation that provide better and/or more precise location of ablation instruments within the heart.

SUMMARY OF THE INVENTION

Devices and methods are disclosed herein for use in diagnostic purposes, such as delivering an imaging agent or for therapeutic purposes such as for delivering various ablation instruments or mapping instruments to regions of the heart, such as to the left atrium, left atrial appendage, or the pulmonary veins.

In one aspect, the deflectable sheath catheters include a deflectable tip section at a distal end and having a varying stiffness along at least a portion of the distal tip section which allows the deflectable tip to deflect along a compound curve. As a result of this tip, the present invention permits ready access to all four pulmonary veins of the left atrium via a single transseptal approach, especially the right inferior pulmonary vein. Moreover, this access is achieved without prolapsing and in a manner that also permits the application of axial force, such that an ablation instrument inserted through the sheath catheter can be both maneuvered into place and held in position during ablation. This is especially useful when the ablation instrument includes a balloon element that must be urged against the ostium of a vein in order to occlude it.

In another aspect, the present invention can include a deflectable sheath catheter having an elongate catheter body with proximal and distal ends, the catheter body comprising multiple flexible segments along its length such at least one (and preferably two or more) of the flexible segments has a different stiffness. The segments of different stiffness are preferably formed by a plurality of polymeric segments of the elongate body having different durometers, and in one embodiment, the durometer of the distal section decreases in the distal direction along at least a portion of the section. The catheter can further include a handle portion at its proximal end, and a deflectable tip section at its distal end wherein the deflectable tip section is deflectable along a compound curve or a spiral curve. While the handle can have a variety of configurations, in one embodiment, it includes a hemostasis valve.

Another aspect of the present invention can include a deflectable sheath catheter having an elongate catheter body with proximal and distal ends such that the catheter body has at least two segments along its length, with at least one segment having a different stiffness. In other embodiments, the catheter can have three, four, five, etc. wall segments. The catheter can further include a stiffening element (e.g., a dilator) which is initially deployed within the catheter body to assist in passing the catheter to the target region. The stiffening element or dilator can subsequently be removed or partially retracted. Moreover, the catheter can include a handle portion at its proximal end, and a deflectable tip section at its distal end wherein the deflectable tip section is deflectable along a compound curve or a spiral curve as a result of the segments of different stiffness.

In another embodiment, the catheter can include at least one braided wire reinforcement layer, where the layer can surround at least a portion of the body length. The layer can be continuous, or alternatively, discontinuous. Moreover, the layer can be varied to provide segments of different stiffness.

In another embodiment, the catheter can further include an actuator that effects deflection of the deflectable tip section. While the actuator can have a variety of configurations, the actuator can further include a lock to fix the deflectable distal end section in a particular curve within its range of movement. Alternatively the actuator can include a pull wire mechanically linking the deflectable distal end section to a proximal handle portion.

In another aspect of the invention, the deflectable tip section of the sheath catheter can be pre-bent, e.g., out of the plane of deflection, such that the operator can deflect the tip section in one plane while the tip itself is oriented in a nonplanar direction. The bend can be formed during manufacturing or the tip can be malleable to permit the user to select a desired bend angle and/or orientation prior to use. The bent tip can be formed at an angle ranging from about 5° to about 90° relative to a central axis of the catheter body in an unflexed state, preferably at an angle ranging from about 10° to about 60° relative to the central axis, and, more preferably in certain applications, at an angle ranging from about 15° to about 45° relative to the central axis of the catheter body.

In a further aspect of the invention, deflectable sheath catheters are disclosed with irrigation holes placed at the distal end of a deflectable tip section. The holes can allow for additional irrigation and fluidic communication between a central lumen in the elongate catheter body and the human vasculature. There is preferably at least one irrigation hole included at the tip section, but the number of holes can be varied depending on the design configuration. In an exemplary embodiment, irrigation side holes can allow for passage of fluids through the deflectable sheath catheter when the distal end of the catheter is in direct contact with the endocardium and a distal tip hole would be occluded.

In another aspect, a deflectable sheath catheter can be adapted for disposition within a heart and includes at least one cardiac ablation instrument which can be deployed through the deflectable sheath catheter to a desired target location. The ablation instrument can further include an optional anchorage element, such as an anchoring balloon, to contact a cardiac structure and secure the device in place.

In one embodiment, the ablation instrument includes a radiant energy delivery element movable within the lumen of a deflectable sheath catheter such that it can be disposed at the desired location and deliver radiant energy through a transmissive region of the instrument to a target tissue site. The ablation instrument can also optionally include a projection balloon that can be employed, alone or together with fluid releasing mechanisms, to provide a blood-free transmission pathway from the energy emitter to the tissue target.

In another embodiment, the ablation instrument includes an ultrasound energy delivery element movable within the lumen of a deflectable sheath catheter such that it can be disposed at the desired location and deliver radiant ultrasound energy through a transmissive region of the instrument to a target tissue site. The ablation instrument can also optionally include a projection balloon and/or a focusing element to reflect the energy emitter to the tissue target.

In another embodiment, the ablation instrument includes microwave energy delivery element movable within the lumen of a deflectable sheath catheter such that it can be disposed at the desired location and deliver radiant microwave energy through a transmissive region of the instrument to a target tissue site. The ablation instrument can also optionally include a projection balloon to provide a focusing element to reflect the energy emitter to the tissue target.

In another embodiment, the ablation instrument includes a cryoablation energy delivery element movable within the lumen of a deflectable sheath catheter such that it can be disposed at the desired location to a target tissue site with a cryogenic surface. The ablation instrument can also optionally include a projection balloon to clear blood from the ablation site and allow delivery of cryoablation of the tissue target. Alternatively, the catheter can include an ablation instrument to deliver ablative fluids, electrical resistive heating or other ablation modalities.

In another aspect, a cardiac ablation assembly is provided that includes a deflectable sheath catheter adapted for disposition within a heart having at least one lumen therein, the catheter having at least one segment of different stiffness to form a compound curve upon deployment and deflection within the heart, and an ablation instrument movable within a lumen of the deflectable sheath catheter such that it can be disposed at a target tissue site to deliver ablative energy. In one embodiment, the ablation instrument can be a radiant energy emitter further comprising a translatory mechanism for positioning the emitter at a selected location within the deflectable sheath catheter. Moreover, the radiant energy emitter can be an ultrasound emitter, hypersound emitter, light emitter, microwave radiation emitter, radio-frequency (RF) radiation emitter, x-ray radiation emitter, ionizing radiation emitter, or a particle beam radiation emitter, depending upon the particular application. In another embodiment, the ablation instrument can be a contact ablation instrument, such as a cryogenic ablation instrument, ablative fluid instruments, or a heating instrument.

In another aspect, a method is provided for cardiac access. The method includes inserting a guide wire into a patient to a target region and then using a guidewire to deliver a deflectable sheath catheter having a deflectable tip into a target region. The method further includes passing the sheath catheter (which can also include an optional internal stiffening element or "dilator") over the guide wire such that the catheter can be directed to the target region. Following removal of the guide wire and dilator, the deflectable tip section of the sheath catheter can be bent, preferably into a compound or a spiral curve, in order to access one or more target regions within the left atrium of the heart. Finally, the tip section can be locked in a bent position, and a medical instrument or treatment fluid is delivered through the catheter to a target site within the heart.

In another method according to the invention, a guide wire is first inserted into the femoral vein and advanced through the inferior vena cava into the right atrium and, optionally, into the left atrium via an atrial septal puncture, where it can be further advanced until it enters a pulmonary vein. A dilator is then positioned within the deflectable sheath catheter and both, together, are positioned over the guide wire and advanced into the heart. If the transseptal puncture has not been performed with the guidewire, the deflectable sheath catheter (preferably with the stiffening element disposed therein) can be used to perform the puncture. The sheath catheter is then advanced into proximity of the target site, e.g., the mouth of a pulmonary vein. The guide wire (and dilator) are then removed and replaced with an ablative instrument, which is positioned by advancing the instrument to contact the ostium of the pulmonary vein with sufficient axial force to create a seal and deliver ablative energy to the target tissue region to ablate tissue and form a conductive block.

In another aspect, a method includes positioning a sheath catheter having a deflectable distal end segment in the left atrium of a heart, orienting said sheath catheter such that an ablation instrument can be delivered through the sheath catheter to a position proximal to a first pulmonary vein, activating the ablation instrument to form a circumferential lesion around the first pulmonary vein, repositioning the sheath catheter by deflecting the distal end segment to another orientation, and activating the ablation instrument to form a circumferential lesion around at least one additional pulmonary vein. In one embodiment, the method further includes repeating the steps of orienting the sheath catheter and activating the ablation instrument until all of the pulmonary veins are isolated by circumferential lesions. In another embodiment, the method further includes positioning (or, alternatively, repositioning) the sheath catheter fluoroscopically, as well as initially deploying the sheath catheter (or the sheath catheter together with a stiffening inner dilator) in the heart over a guide wire. Moreover, the method includes using a sheath catheter together with the stiffening inner dilator to create a septal puncture in order to gain access to the left atrium of the heart.

In another embodiment, the step of activating the ablation instrument further includes positioning a radiant energy emitter at a selected location within a balloon catheter that is deployed within the heart via the sheath catheter and then activating the radiant energy emitter. The radiant energy emitter can be a variety of energy emitters, such as an ultrasound emitter, a hypersound emitter, a light emitter, a microwave radiation emitter, a radio-frequency (RF) radiation emitter, an x-ray radiation emitter, an ionizing radiation emitter, and particle beam radiation emitter.

In one embodiment, the step of activating the radiant energy emitter further includes activating a light emitting element to expose the target region to light energy to induce photocoagulation of cardiac tissue within the target region. Alternatively, the step of activating the radiant energy emitter can include activating a light emitting element to expose the target region to light energy to induce a continuous lesion in the cardiac tissue, activating a light emitting element having a beam-forming optical waveguide to expose the target region to an annular beam of light energy to induce a circumferential lesion in cardiac tissue, and/or activating a light emitting element generating photoablative radiation at a desired wavelength ranging from about 800 nm to about 1000 nm, or from about 915 nm to about 980 nm.

Moreover, the step of activating the radiant energy emitter can further comprise activating an ultrasound emitting element to expose the target region to acoustic energy to induce photocoagulation of cardiac tissue within the target region, or, alternatively, activating a radiation emitting element to expose the target region to at least one form of radiant energy selected from the group consisting of microwave, x-ray, gamma-ray and ionizing radiation to induce photocoagulation of cardiac tissue within the target region.

In another embodiment, the method further includes inflating a projection balloon to clear blood from a transmission pathway between the energy emitter and a target region of cardiac tissue, and determining whether a clear transmission path has been established between the radiant energy emitter and the target tissue based on reflectance measurements by an optical sensor disposed within the lumen of the deflectable sheath catheter. Alternatively, the method further includes measuring at least two different wavelengths of reflected light collected by the optical sensor to determine whether a projection path exists.

In another embodiment, the step of activating the ablation instrument further includes deploying a contact ablation instrument within the heart via the sheath catheter, positioning the contact ablation instrument at a selected location and then activating the contact ablation instrument. While the contact ablation instrument can have a variety of configurations, in an exemplary embodiment the contact ablation instrument is selected from the group consisting of cryogenic ablation instruments, ablative fluid instruments and heating instruments.

In another aspect, a method for ablating tissue about an ostium of a right inferior vein of a heart includes positioning a sheath catheter having a deflectable distal end segment with a bent tip element in the left atrium of a heart, causing the distal end segment to deflect in a compound curve as the catheter is advanced towards an ostium of a right inferior vein, orienting said sheath catheter such that an ablation instrument can be delivered through the sheath catheter to a position proximal to the right inferior vein, and activating the ablation instrument to form at least one lesion about the right inferior vein. In one embodiment, the method can further include initially deploying the sheath catheter in the heart over a guide wire, or initially deploying the sheath catheter together with a stiffening inner dilator over a guide wire. Moreover, the method can include using the sheath catheter together with the stiffening inner dilator to create a septal puncture in order to gain access to the left atrium of the heart.

In another embodiment, the step of activating the ablation instrument further includes positioning a radiant energy emitter at a selected location within a balloon catheter that is deployed within the heart via the sheath catheter and then activating the radiant energy emitter. The radiant energy emitter can have a variety of configurations, such as an ultrasound emitter, a hypersound emitter, a light emitter, a microwave radiation emitter, a radio-frequency (RF) radiation emitter, an x-ray radiation emitter, an ionizing radiation emitter, a particle beam radiation emitter, or a focused acoustic energy emitter.

In another embodiment, the step of activating the ablation instrument further includes deploying a contact ablation instrument within the heart via the sheath catheter, positioning the contact ablation instrument at a selected location and then activating the contact ablation instrument. While the contact ablation instrument can have a variety of configurations, in an exemplary embodiment it is selected from the group consisting of cryogenic ablation instruments, ablative fluid instruments and heating instruments.

In yet another aspect of the invention, the deflectable sheath catheter of the present invention permits access to all four pulmonary veins. The compound curved shape and/or the bent tip structures make the sheath catheter of the present invention highly maneuverable, permitting the sheath catheter, for example, to arch over the roof of the left atrium in order to direct an ablation instrument to the ostia of the right pulmonary veins, which are particularly difficult to reach with conventional ablation instruments. Therefore, the present invention addresses current problems associated with cardiac access, in particular accessing the left atrium and inferior pulmonary veins, particularly, the right inferior pulmonary vein of the human heart.

In another aspect of the invention, a cardiac ablation instrument assembly is disclosed having a deflectable sheath catheter adapted for disposition within a heart and at least one ablation instrument which can be deployed via a proximal hemostasis valve and through the deflectable sheath catheter to a desired target location. A deflectable sheath catheter is provided (and, optionally a dilator as previously described above) having a handle at a proximal end and a deflectable tip section at a distal end. The deflectable tip section provides access to the heart and target region of cardiac tissue and allows an ablation instrument to reach the target cardiac tissue, preferably in the left atrium of the heart to access the pulmonary veins for the treatment of atrial fibrillation. The sheath is able to "point" the ablation device at the ostium of the pulmonary vein and the ablation instrument is advanced to the target tissue and axial force can be applied to maintain contact with the target tissue during ablation of the tissue.

In one embodiment, the ablation instrument is deliverable through the deflectable sheath catheter and includes an energy emitter element that is independently movable within a lumen of the ablation instrument following the deployment of the instrument, such that the energy emitter can be disposed at the desired location to deliver radiant energy through a transmissive region of the instrument to a target tissue site. The ablation instrument can further include a projection balloon, alone or together with fluid releasing mechanisms, to provide a blood-free transmission pathway from the energy emitter to the tissue target.

In another embodiment, the ablation instrument includes at least one anchorage element which can be deployed at the desired location to contact a cardiac structure and secure the ablation instrument in place. The instrument again includes an energy emitter element movable within the lumen of the ablation instrument, following deployment of the instrument via the deflectable sheath catheter. A projection balloon can again be employed, alone or together with fluid releasing mechanisms, to provide a blood-free transmission pathway from the energy emitter to the tissue target.

BRIEF DESCRIPTION OF THE DRAWINGS

The invention will be more fully understood from the following detailed description taken in conjunction with the accompanying drawings, in which like reference numerals designate like parts throughout the figures, and wherein.

DETAILED DESCRIPTION

Figure 1:
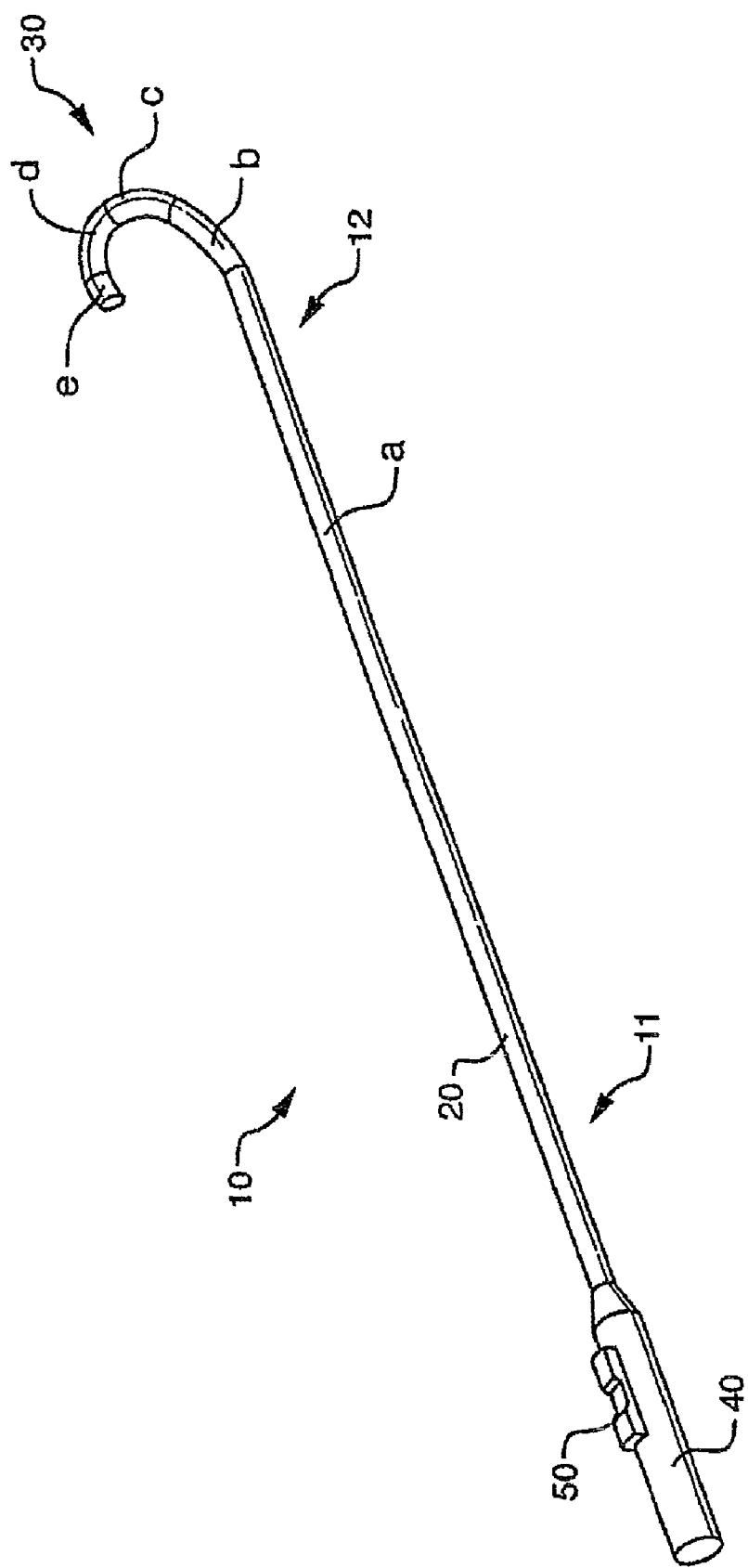
FIG. 1 is a schematic view of an embodiment of the present invention showing a deflectable sheath catheter with a handle and a deflectable tip section.

Certain exemplary embodiments will now be described to provide an overall understanding of the principles of the structure, function, manufacture, and use of the methods and devices disclosed herein. One or more examples of these embodiments are illustrated in the accompanying drawings. Those skilled in the art will understand that the methods and devices specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides devices and methods for the treatment of atrial fibrillation. In one embodiment a deflectable sheath catheter includes an elongate catheter body having proximal and distal ends, the distal end having a distal tip region that includes a plurality of flexible segments with varying degrees of stiffness. A handle portion can be located at the proximal end of the catheter body to provide a steering mechanism that causes the distal tip region to deflect according to a compound curve or a spiral curve. Although described in connection with cardiac ablation procedures, it should be clear that the devices and methods of the present invention can be used for a variety of other procedures where treatment with radiant energy is desirable, including laparoscopic, endoluminal, perivisceral, endoscopic, thoracoscopic, intra-articular, and hybrid approaches.

Before discussing the features of the devices and methods disclosed herein, it should be understood that:

As used herein, the term "balloon" encompasses deformable hollow shapes that can be inflated into various configurations such as a balloon, circle, tear drop, or any other shape depending upon the requirements of the particular cavity. Moreover, the balloon can also have any number (i.e., multiple) of chamber configurations. The balloon elements can also have a variety of forms, and can be either elastic or simply capable of unfolding or unwrapping into an expanded state.

As used herein, the term "catheter" encompasses any hollow instrument capable of penetrating body tissue or interstitial cavities and providing a conduit for selectively injecting a solution or gas, including without limitation, venous and arterial conduits of various sizes and shapes, bronchoscopes, endoscopes, cystoscopes, culpascopes, colonoscopes, trocars, laparoscopes and the like. The term "catheter" is also intended to encompass any elongate body capable of serving as a conduit for one or more of the ablation, expandable or sensing elements described herein, e.g., energy emitters, balloons and/or endoscopes. Specifically, in the context of coaxial instruments, the term "catheter" can encompass either the outer catheter body or sheath or other instruments that can be introduced through such a sheath. The use of the term "catheter" should not be construed as meaning only a single instrument but rather is used to encompass both singular and plural instruments, including coaxial, nested, and other tandem arrangements. Moreover, the terms "deflectable sheath catheter" or "steerable catheter" or "guiding catheters" are used interchangeably to describe catheters having at least one lumen through which instruments or treatment modalities can pass. Such deflectable sheath catheters can be used, for example, for transeptal passage of ablation instruments and the like into the left atrium of the heart.

As used herein, the term "compound curve" refers to a curve that can have a variable radius of curvature along different portions of the curve. The curvature can increase or decrease and can be a continual change or take the form of segmented arcs where the radius of curvature is constant over a given length but varies from one arc to the next. The change in curvature of the compound curve can also be progressive or varying in accordance with other patterns.

As used herein, the terms "circumferential" and/or "curvilinear," including derivatives thereof, are intended to mean a path or line which forms an outer border or perimeter that either partially or completely surrounds a region of tissue, or separate one region of tissue from another. Further, a "circumferential" path or element may include one or more of several shapes, and may be for example, circular, annular, oblong, ovular, elliptical, semi annular, or toroidal.

As used herein, the term "continuous" in the context of a lesion is intended to mean a lesion that substantially blocks electrical conduction between tissue segments on opposite sides of the lesion.

As used herein, the term "lumen," including derivatives thereof, in the context of biological structures, is herein intended to mean any cavity or lumen within the body which is defined at least in part by a tissue wall. For example, cardiac chambers, the uterus, the regions of the gastrointestinal tract, the urinary tract, and the arterial or venous vessels are all considered illustrative examples of body spaces within the intended meaning. The term "lumen" including derivatives thereof, in the context of catheters is intended to encompass any passageway within a catheter instrument (and/or track otherwise joined to such instrument that can serve as a passageway) for the passage of other component instruments or fluids or for delivery of therapeutic agents or for sampling or otherwise detecting a condition at a remote region of the instrument.

As used herein, the term "radiant energy" includes ultrasound, focused ultrasound, hypersound, and other forms of acoustic energy as well as light (including visible, ultraviolet and infrared radiation), microwave radiation, radio-frequency (RF) radiation, x-ray radiation, ionizing radiation and other forms of electromagnetic or particle beam or radiation as well as focused acoustic energy.

As used herein, the term "ablative energy" is intended to encompass any and all forms of radiant energy (as described above) as well as contact ablation mechanisms, such as the application of heat by conductive or convective means and/or the application of cryogenic treatments and/or the use ablative chemical or thermal fluids (either gaseous or liquid) to form a lesion.

As used herein, the term "transparent" includes those materials that allow transmission of energy through, for example, the primary balloon member. While a variety of materials can be used, such as transparent materials include fluoropolymers, for example, fluorinated ethylene propylene (FEP), perfluoroalkoxy resin (PFA), polytetrafluoroethylene (PTFE), and ethylene-tetrafluoroethylene (ETFE) or polyester resins including polyethylene teraphathalate (PET), the preferred transparent material should not significantly impede (e.g., result in losses of over 20 percent of energy transmitted) the energy being transferred from an energy emitter to the tissue or cell site As used herein, the "Shore (Durometer) test" refers to a commonly used method of measuring the resistance of plastics toward indentation and providing an empirical hardness value. Shore Hardness, using either the Shore A or Shore D scale, is the preferred method for rubbers/elastomers and is also commonly used for 'softer' plastics such as polyolefins, fluoropolymers, and vinyls. The Shore A scale is used for 'softer' rubbers while the Shore D scale is used for 'harder' ones. Unless otherwise noted, stiffness ratings referred herein are based on the Shore (Durometer) test.

As used herein, a "transseptal approach" refers to a surgical technique that involves the puncture of the intra-atrial septum followed by advancement of a catheter into the left atrium and left ventricle.

As used herein, the term "vessel" or "blood vessel" includes, without limitation, veins, arteries, and various chambers or regions of the heart, such as the atria, ventricles, coronary sinus, vena cava and, in particular, the ostia or atrium of the pulmonary veins.

As used herein, the terms "visual," "visualize" and derivatives thereof describe both human and machine uses of reflectance data. Such data can take the form of images visible to a clinician's eye or any machine display of reflected light, e.g., in black & white, color or so-called "false color" or color enhanced views. Detection and display of reflected energy measurements outside the visible spectrum are also encompassed. In automated systems such visual data need not be displayed but rather employed direct by a controller to aid in the ablation procedure.

FIGS. 1 to 33 illustrate embodiments of the present invention relating to devices and methods for percutaneous access to the heart, and in particular, the left atrium via a transseptal approach. FIG. 1 shows one embodiment of a deflectable sheath catheter 10 having proximal and distal ends 11, 12 connected by an elongate catheter body 20. While the proximal and distal ends 11, 12 can have a variety of configurations, as shown the proximal end 11 includes a handle portion 40 and a variable locking actuator 50, and the distal end 12 includes a deflectable tip section 30 (the handle 40 and the tip 30 will be discussed in more detail below).

The catheter body 20 can have any configuration suitable for insertion into and/or through a vein or artery, such as circular, oblong or ovular, however as shown the catheter body 20 is ovular. The catheter body 20 can also have at least one lumen 21 formed therein and extending therethrough. While the lumen 21 can also be formed in a variety of locations within the catheter body 21, preferably the lumen 21 is centrally located. The lumen 21 can have a variety of shapes, such as circular, oblong or ovular, however in an exemplary embodiment the lumen 21 has a shape that is complementary to the shape of the catheter body 20, e.g., ovular.

The elongate catheter body 20 can include any number of flexible wall segments to allow for movement thereof. For example, the catheter body 20 can be one continuous segment. Alternatively, the catheter body 20 can have any number of flexible segments, such as two, three, four, five, six, etc., at least one of which has a different stiffness than the others. As shown, the catheter body 20 has five flexible segments a, b, c, d, and e. The flexible segments a, b, c, d, and e can have any stiffness configuration that allows the catheter 10 to move within the heart or surrounding area, however in an exemplary embodiment each flexible segment a, b, c, d, and e has a different stiffness. The variation of the stiffness of the flexible segments can be random or along a gradient and, as shown in FIG. 1, the stiffness of the flexible segments a, b, c, d, and e can be a gradient of distally decreasing stiffness along the length of the body 20, e.g., segment a can have a stiffness rating of "72 D," segment b can have a stiffness rating of "63 D," segment c can have a stiffness rating of "55 D," segment d can have a stiffness rating of "40 D," and segment e can have a stiffness rating of "35 D." One skilled in the art will appreciate that the variation in the stiffness of the segments a, b, c, d, and e allows the deflectable tip to deflect along a compound curve, or alternatively, a spiral curve.

Each segment can also have a variety of lengths, preferably ranging from 1 mm to 100 mm. Each segment can have the same length, or each section can vary in length from one another by either random variations or on a continuous gradient (such as the distal decrease in length shown in FIG. 1). Moreover, the deflectable tip section 30 can be varied in length, however in an exemplary embodiment is in the range of about 20 mm to 20 cm.

The elongate catheter body 20 can be made from a variety of flexible, biocompatible polymers such that different stiffness ratings are able to be formed. One such polymer that allows for the formation of different stiffness ratings is Pbax plastic. The catheter body 20 can also include an interior lining made from the same or a different polymer material. Moreover, different portions of the catheter body 20 can be made of different materials, e.g., the deflectable tip 30 can be made from the same or different material as the elongate catheter body 20 described above.

FIGS. 2 to 9 further illustrate various components of the catheter of FIG. 1, such the handle 40 and the deflectable tip 30, as well as various features of the catheter that can assist a surgeon in accessing the desired tissue.

Figure 2:
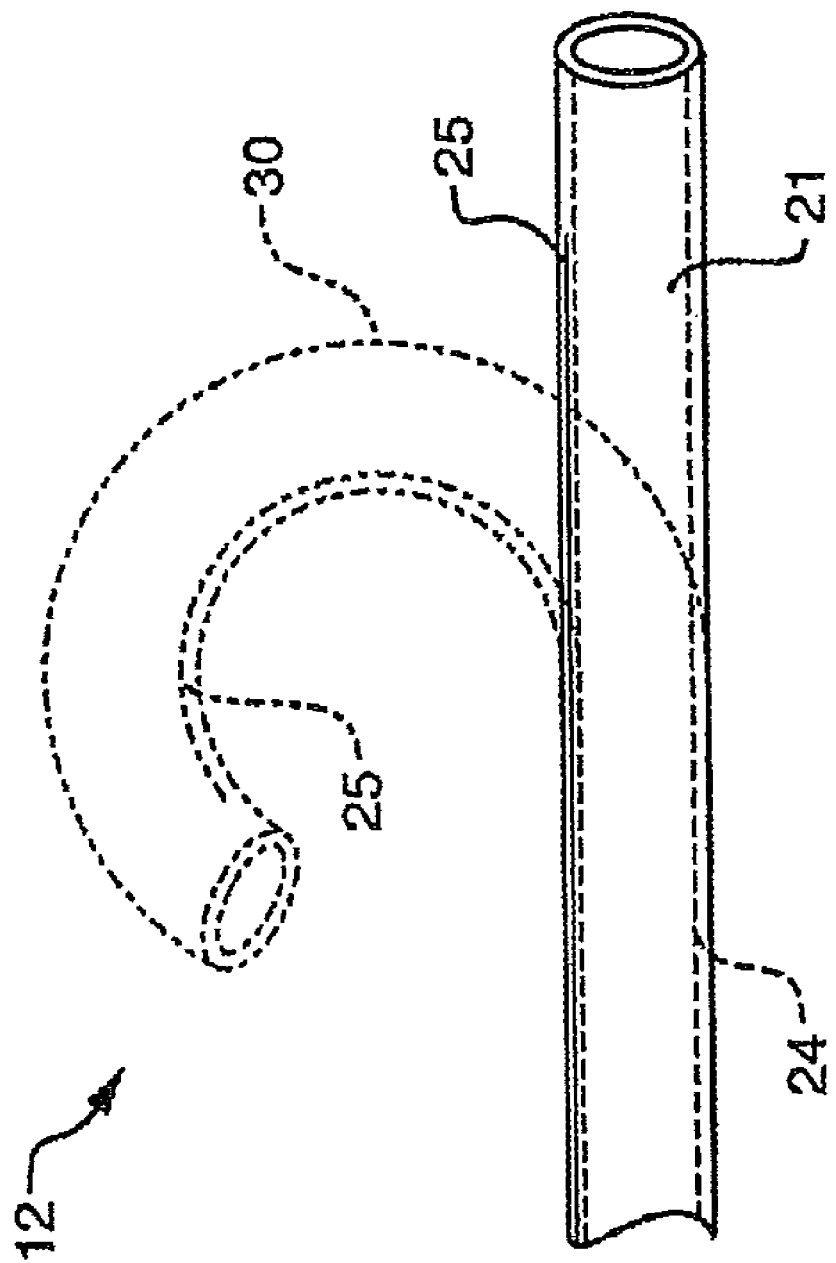
FIG. 2 is a close-up view of an embodiment of the present invention showing the deflectable tip section.

FIG. 2 illustrates the distal end 12 of the deflectable sheath catheter. As shown the distal end 12 includes a pull wire 25 that extends between a variable locking actuator (such as variable locking actuator 50 shown in FIG. 1) on the handle portion 40 (such as handle portion 40 shown in FIG. 1) and the tip 30 such that the tip 30 that is movable within the wall 24 of the elongate catheter body 20.

The pull wire 25 can have a variety of configurations, however in an exemplary embodiment, the pull wire 25 is preferably cylindrical in shape and can be sized to fit a channel within the wall 24 of the elongate catheter body 20 without communication with the central lumen 21. The pull wire 25 can also be attached to the actuator 50 and the deflectable tip 30 in a variety of ways, and in an exemplary embodiment, the pull wire 25 can be fastened at its proximal end to the actuator 50 (shown in FIG. 1) and at the distal end to the deflectable tip section 30. A variety of both fixed and removable fastening means can be used to mate the pull wire 25 with both the actuator 50 and the deflectable tip 30, such as clamps, screws, bolts, anchors, and hooks. Alternatively, the distal end of the pull wire 25 can be welded to a stainless steel ring which is embedded in the distal end of the catheter body 20.

Upon movement of the pull wire 25, the deflectable tip section 30 can deflect to varying degrees depending upon the amount of lateral movement of the pull wire 25. In an exemplary embodiment, the deflectable tip section can move in the range of about 5° to about 270°, more preferably from about 10° to about 200°.

Figure 3B:
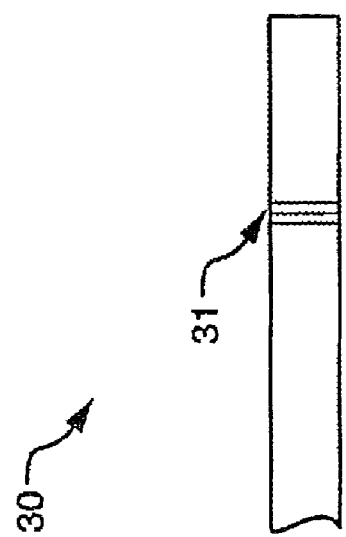
FIG. 3B is a top perspective view of the deflectable tip section of FIG. 3A.
Figure 3A:
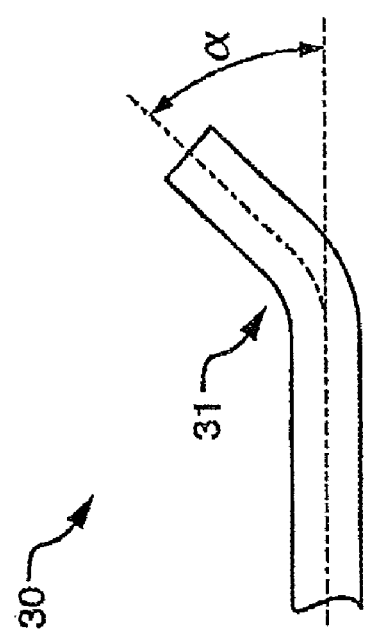
FIG. 3A is a schematic, perspective view of another embodiment of the present invention showing a variation of a deflectable tip section.

FIGS. 3A and 3B show another embodiment of the present invention where the deflectable tip section 30 can be preformed or bent, prior to insertion into a patient, through one or more planes. While the bend 31 can be any degree that allows a surgeon to access the heart, in an exemplary embodiment, the bend 31 is formed in a posterior direction in the range of about 20° to about 90° relative to the heart (shown as angle α). Moreover, angle α can be between about 5° to about 90° relative to the central axis of the catheter in an unflexed state, from about 10° to about 60° relative to the central axis of the catheter in an unflexed state, or, more preferably between about 15° to about 45° relative to the catheter in an unflexed state. One skilled in the art will appreciate that such a bend 31 facilitates more effective access to the heart, especially to the superior and inferior pulmonary veins of the heart.

The bend 31 of the deflectable tip section 30 can made in any manner known in the art that allows it to maintain its position throughout the range deflection relative to its plane of displacement. For example, the bend 31 can be formed during manufacturing by molding or extrusion. Alternatively, the bend 31 can be formed prior to use, that is the bend 31 can be formed from a shape memory metal such as NITINOL (as acronym for Nickel Titanium Naval Ordnance Laboratory) family of intermetallic materials, which contain a nearly equal mixture of nickel (55% by weight) and titanium.

One skilled in the art will appreciate that the bent tip 31 is particularly useful in accessing all four pulmonary veins because the ostium of these veins do not all lie in a single plane of deflection.

Moreover, the bend 31 can be used in conjunction with a pull wire 25, similar to that as discussed with respect to FIG. 2, and one skilled in the art will appreciate that the combination of the pull wire 25 and the bend 31 allow a surgeon precision control to access various locations within the heart.

Figure 4A:
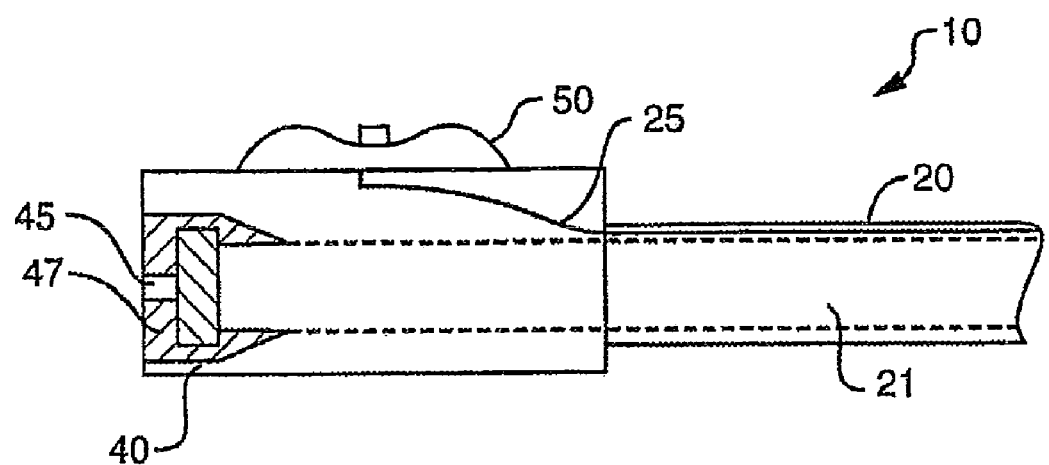
FIG. 4A is a schematic view of an embodiment of the present invention showing a handle portion and a variable locking deflection actuator.
Figure 4B:
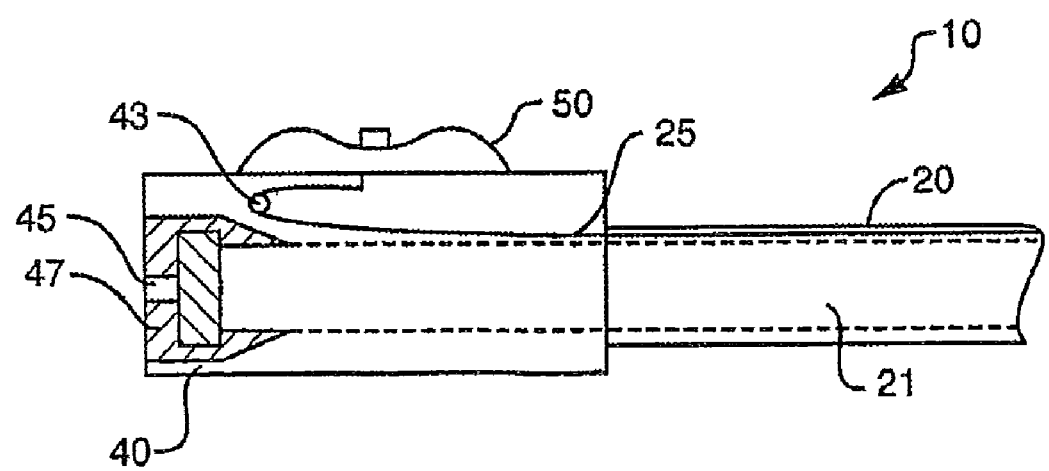
FIG. 4B is a schematic view of another embodiment of the present invention showing a variation of a handle portion and an actuator.
Figure 4C:
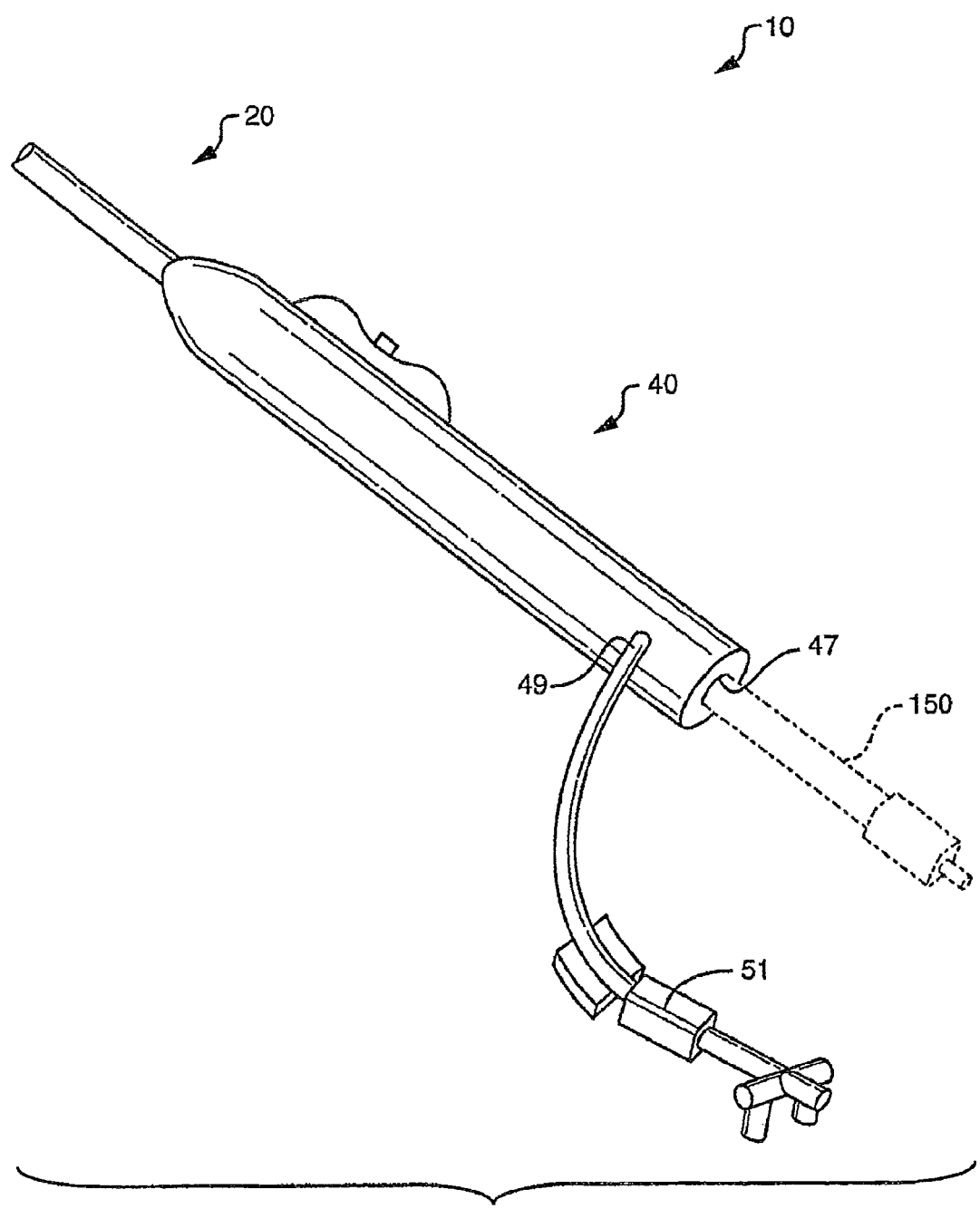
FIG. 4C is a schematic view of another embodiment of the present invention showing a handle portion having a hemostasis valve.

FIGS. 4A to 4C illustrate a deflectable sheath catheter 10 having one embodiment of a handle portion 40 with a variable locking actuator 50, features to connect the actuator 50 to a pull wire (such as pull wire 25 discussed above), as well as various port and valve assemblies.

The handle portion 40 can have any configuration known in the art, however as shown, the handle 40 can include a central lumen 45 connected to lumen 21 of the elongate catheter body 20. Lumen 45 can have a variety of configurations, e.g., circular, oblong or ovular, however in an exemplary embodiment the lumen 45 has a shape that is complementary to the shape of the lumen 21 of the elongate catheter body 20 (that is, ovular). The lumen 45 can also terminate in an end port 47 (as will be discussed in more detail below).

While the handle portion 40 can be either fixedly or removably mated to the elongate catheter body 20, in an exemplary embodiment, the handle portion 40 is removably mated to the catheter body 20 by any means known in the art such as a nut and bolt assembly. Alternatively, the elongate catheter body 20 can extend into the handle portion 40 such that it can connect to the central lumen 45 at a point proximal to the distal end of the handle portion 40. The handle portion 40 can also include means to connect a pull wire 25 with the actuator 50.

The variable locking actuator 50 can have any configuration that causes the pull wire 25 to move in a lateral direction along the elongate catheter body 20. In an exemplary embodiment, the actuator 50 can be configured such that it can lock in place, thereby allowing the deflectable tip section 30 to remain in a deflected position at various points throughout its range of movement. The positions at which the actuator 50 can lock can be determined by the mechanical increments designed into the variable locking actuator 50 and handle portion 40. While the mechanism can be configured to lock the actuator 50 in a variety of increments, in one embodiment the mechanism can be configured to lock the actuator 50 at 1° of tip deflection, or every 5° of tip deflection.

The variable locking actuator 50 can also include a variety of fastening means to either fixedly or removably mate with the pull wire 25, and such means can be either a direct or an indirect connection. As shown in FIG. 4A, the pull wire 25 can connect to the variable locking actuator 50 via direct connection. In use, as the actuator 50 is displaced in a distal to proximal direction, the pull wire 25 is displaced in the same direction and thus the deflectable tip section 30 is deflected a desired amount. To return the deflectable tip section 30 to its un-deflected position, the actuator 50 is moved in a proximal to distal direction, thus moving the pull wire 25 in the same direction and allowing the tip 30 to uncoil. Alternatively, the pull wire 25 can be indirectly connected to the actuator 50 via a pulley mechanism 43 as shown in FIG. 4B. While the pulley mechanism 43 can have a variety of configurations, in an exemplary embodiment the pulley mechanism 43 can be housed in the handle portion 40 such that the pull wire 25 can wrap around the pulley 43 and connect to the actuator 50. In use, the actuator 50 is displaced in a proximal to distal direction in order to deflect the tip section 30 and the reverse operation can uncoil the tip 30.

The handle portion 40 can also have a variety of port and valve assemblies attached thereto. For, example, as shown in FIG. 4C, an exemplary sideport and valve access assembly can include at least one fluid access sideport 49 and at least one valve 51. The sideport and valve assembly can be either fixedly or removably mated to the handle portion 40 in a variety of ways, such as by adhesives, press fit, etc. Moreover, the sideport and valve assembly can be mated to the handle portion 40 such that the assembly is in fluid communication with the central lumen 45 of the handle 40.

While the sideport 49 can have a variety of configurations, in an exemplary embodiment the sideport 49 is sized such that it can carry saline or other appropriate fluids, such as a heparin drip, contrast solution or other medications or agents, into one or more lumens (such as lumen 21) within catheter body 20 for the treatment and/or diagnosis of ailments afflicting the human vasculature. The valve 51 can be any valve known in the art such as a manual valve, a one-way value, a two-way value or a stop valve.

As noted above, the central lumen 45 of the handle 40 can terminate in an end port 47. While the end port 47 can have a variety of configurations, in an exemplary embodiment the end port 47 includes a hemostasis valve at its proximal end to allow for the insertion of other medical instruments into the handle portion 40 and subsequently into the lumen 21 of the elongate catheter body 20.

The hemostasis valve can have a variety of shapes and sizes depending upon the particular procedure and instrumentation required, however in an exemplary embodiment the hemostasis valve can be sized in the range of about 2.5 Fr. to about 15 Fr. One skilled in the art will appreciate that the hemostasis valve allows instruments (such as dilator 150 shown in phantom) to be introduced through the deflectable catheter 40 without blood loss through the proximal end of the handle 40 while also preventing the introduction of air into the deflectable catheter 40 using insertion of devices through the hemostasis valve.

One skilled in the art will appreciate that the handle portion 40 above can be made out of a variety of materials, such as plastic, metal, or any suitable material known in the art.

Figure 5:
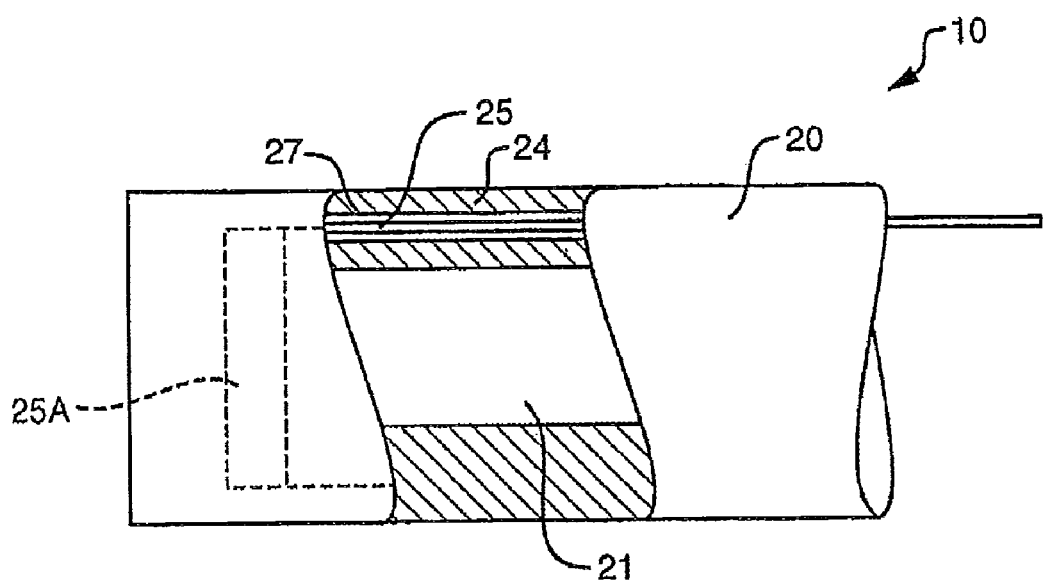
FIG. 5 is a schematic, perspective view of an embodiment of the present invention showing an elongate catheter body with a pull wire and an imbedded pull ring.
Figure 6:
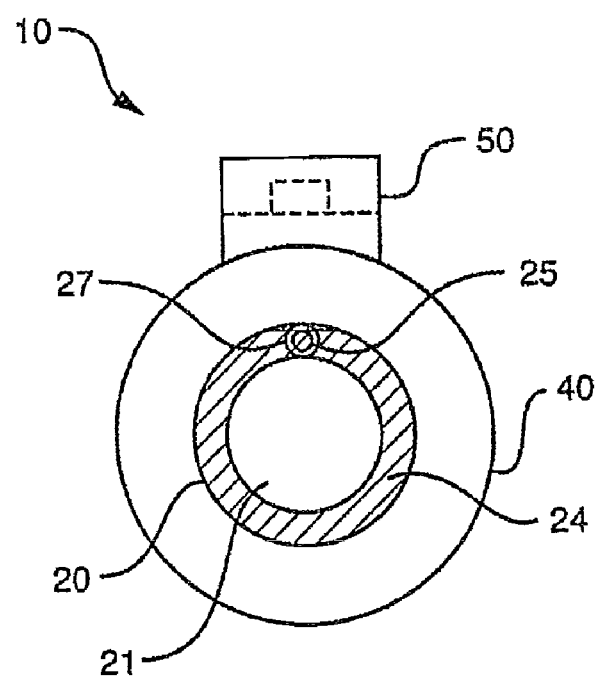
FIG. 6 is a schematic, end view of an embodiment of the present invention showing an elongate catheter body with a pull wire and an axially centered lumen.

FIGS. 5 and 6 illustrate another embodiment of the catheter 10 where the pull wire 25 is disposed within the wall 24 of the elongate catheter body 20. While the pull wire 25 can be disposed within the wall of the elongate catheter body 20 in a variety of ways, as shown the pull wire 25 is disposed within a chamber 27 formed within the wall 24, such that the pull wire 25 is not in communication with the catheter body 20 or the central lumen 21 of the catheter 20. Moreover, the distal end of the pull wire 25 can be anchored to the wall 24 of the catheter body 20, preferably with the aid of an anchor ring 25A as shown, to help distribute the tensile forces exerted during deflection.

While the chamber 27 can be formed in a variety of locations within the wall, as shown in FIG. 5B, the chamber 27 is located on the same side as the variable locking actuator 50 in handle portion 40. Thus, in use, the deflectable tip section 30 deflects angularly toward the locking actuator 50 (as a result the tip 30 will deflect upwards). Alternatively (not shown), the pull wire can be located in another area of the wall such that the tip section can deflect angularly in a different direction. In yet another embodiment (also not shown), a deflectable sheath catheter can have two pull wires, each pull wire disposed in different chambers of the wall. While each pull wire can be attached to the actuator either in tandem or separately, in an exemplary embodiment each pull wire can be attached to the actuator separately to allow the deflectable tip section to deflect in different directions relative to the catheter body.

Figure 7:
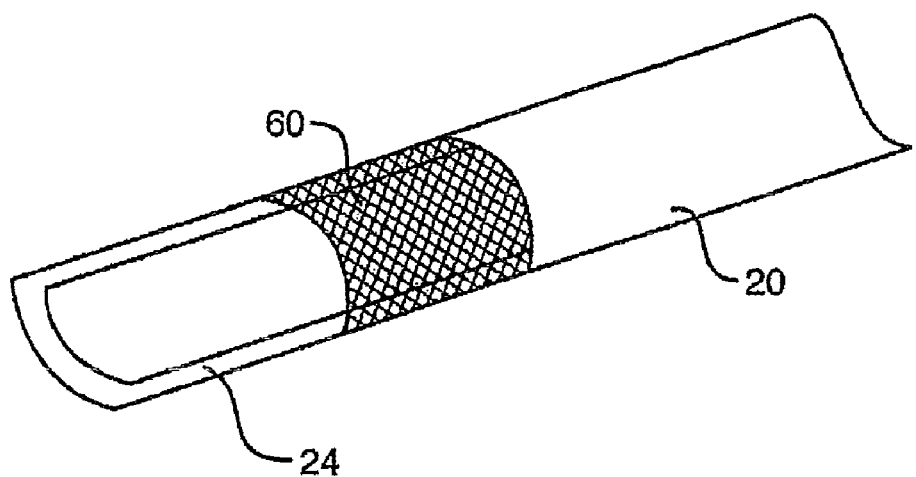
FIG. 7 is a schematic, perspective view of an embodiment of the present invention showing an elongate catheter body having a braided sheath section.

FIG. 7 shows another embodiment of the present invention where the wall 24 of the elongate catheter body 20 includes a wire sheath or braid section 60 for reinforcement. While the braid section 60 can have any configuration that aids the structural reinforcement of the elongate catheter body 20, as shown the braid section 60 is woven in a crisscross pattern. The braid section 60 can also have varying strength and thickness depending upon the amount of flexibility desired in the elongate catheter body 20, and can be applied in a various patterns with different densities to achieve the desired variable stiffness/flexibility properties.

The braid section 60 can be placed at a variety of locations along the catheter body 20, and in an exemplary embodiment it is wrapped around the wall 24 of the elongate catheter body 20. Moreover, the braid section 60 can be continuous, along the entire length of the wall 24 of the elongate catheter body 20, or the braid section 60 can be discontinuous along the length of the wall 24 of the elongate catheter body 20 (that is, the braid section 60 can be located in sections around the wall 24 of the elongate catheter body 20, as desired, with sections of no braid located in-between the braid sections). In an exemplary embodiment, the braid section 60 can stop prior to the deflectable tip section 30 to allow the tip section 30 to deflect as previously described.

One skilled in the art can appreciate that the braid section 60 can be made from any material that can provide sufficient reinforcement to the catheter body 20, including various metal or metal alloys, or various polymers.

Figure 8:
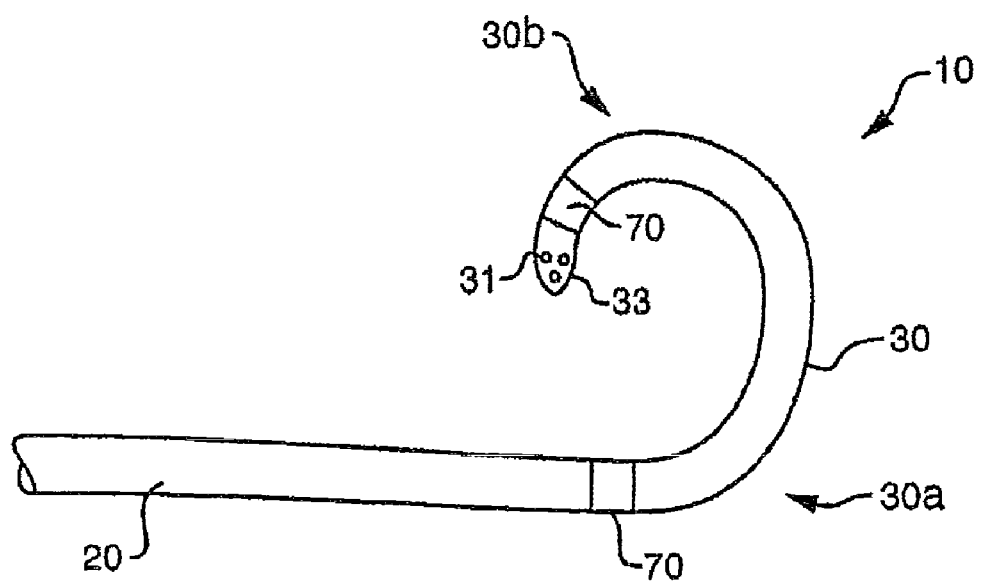
FIG. 8 is a schematic, perspective view of an embodiment of the present invention showing a deflectable tip section having radiopaque bands and irrigation ports.

FIG. 8 shows an embodiment of the present invention where the catheter 10 has at least one radio opaque marker band 70 and at least one irrigation hole 31 located at the distal end of the catheter 10. While the catheter 10 can have any number of marker bands 70, as shown the catheter 10 has two marker bands 70. The marker bands 70 can be located in a variety of locations along the catheter 10, however the marker bands 70 are preferably located at the proximal end 30a of the deflectable tip section 30 and near the distal end 30b of the tip section 30. Alternatively, for catheters having a taper formed at the distal end thereof (such as taper 33 discussed below), the marker bands can be formed proximal to said taper.

The marker bands 70 can have any size that allows the marker bands 70 to be visible when viewed under x-ray or other biomedical imagery device or process known in the art. One skilled in the art will appreciate that any radio opaque material can be used to form the marker bands, however in an exemplary embodiment the marker bands can be formed of gold. Moreover, the catheter material itself may be rendered radio opaque by compounding the polymer used with barium sulfate ($BaSO_4$) in a concentration of about 20-40 percent.

As noted above, the catheter 10 can have any number of irrigation holes 31 formed therein to allow for additional irrigation and fluidic communication between the central catheter lumen 21 in the elongate catheter body 20 and the human vasculature. As shown the catheter 10 has three holes 31. While the irrigation holes 31 can be located in a variety of locations on the catheter 10, in an exemplary embodiment at least one irrigation hole 31 is formed in the tip section 30 of the catheter 10. Alternatively, at least one hole 31 can be formed on the side of the catheter body 20, or, alternatively the tip section 30 of the catheter 10. The holes 31 can have any size such that there can be fluidic communication between the central catheter lumen 21 in the elongate catheter body 20 and the human vasculature. One skilled in the art will appreciate that the holes 31 can also allow the passage of fluids through the central lumen 21 in the event that the distal opening of the central lumen 21 is occluded by tissue contact or thrombus.

Figure 9:
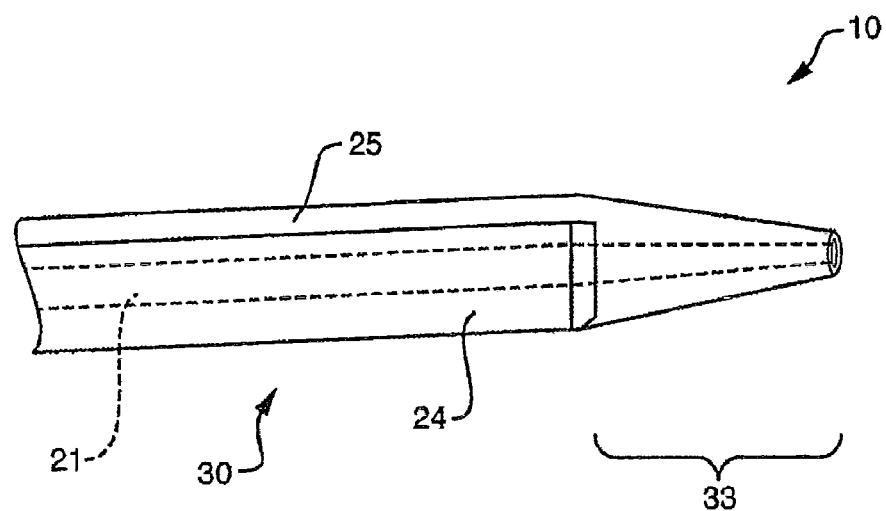
FIG. 9 is a schematic, perspective view of another embodiment of the present invention showing a tapered deflectable tip section.

FIG. 9 shows another embodiment of a catheter with a deflectable tip section 30 having a distal taper 33. While the taper 33 can have a variety of configurations, the taper 33 can have a length and amount such that the deflectable tip section 30 can be navigated through an artery or vein with ease. Moreover, one skilled the art will appreciate that the taper 33 allows the tip section 30 to be made from a softer material thus rendering it atraumatic to delicate vascular structures and endocardial tissue.

Figure 10:
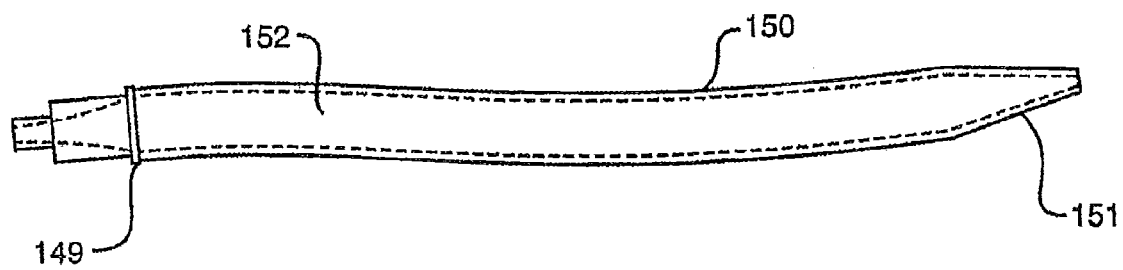
FIG. 10 is a schematic view of an embodiment of the present invention showing a dilator or stiffening element disposed with the sheath catheter.

A variety of devices can be used with the catheter described herein such as a dilator or an ablation instrument. FIG. 10 shows one embodiment of the catheter including a dilator 150. The dilator 150 can have any configuration that allows it to be passed through the catheter and over a guide wire and into the heart, however, as shown the dilator 150 has proximal and distal ends 149, 151, and can include a central lumen 152 formed therein. The central lumen 152 can have any shape and size, such as circular, ovular or oblong, however here the central lumen 152 corresponds in shape to the shape of the catheter (e.g., is ovular), and is adapted to fit snugly within the central lumen of the deflectable sheath catheter, allowing easy insertion of an atrial septum puncture instrument through the vasculature. One skilled in the art will appreciate that the close fitting nature of the dilator 150 within the deflectable catheter can prevent the tip 30 of the deflectable catheter from prolapsing if axial forces are encountered crossing the atrial septal puncture site.

The dilator 150 can also have a variety of other features to assist in its placement. For example, the distal end 157 of the dilator 150 can be tapered for ease of transition within a vein or vessel. The dilator 150 can also be configured to have radio opaque markings, similar to the marker bands 70 described above, at various points along its length or it can be made entirely from a radio opaque material. Alternatively, the dilator can be made from a polymer material and can be biocompatible.

Figure 11:
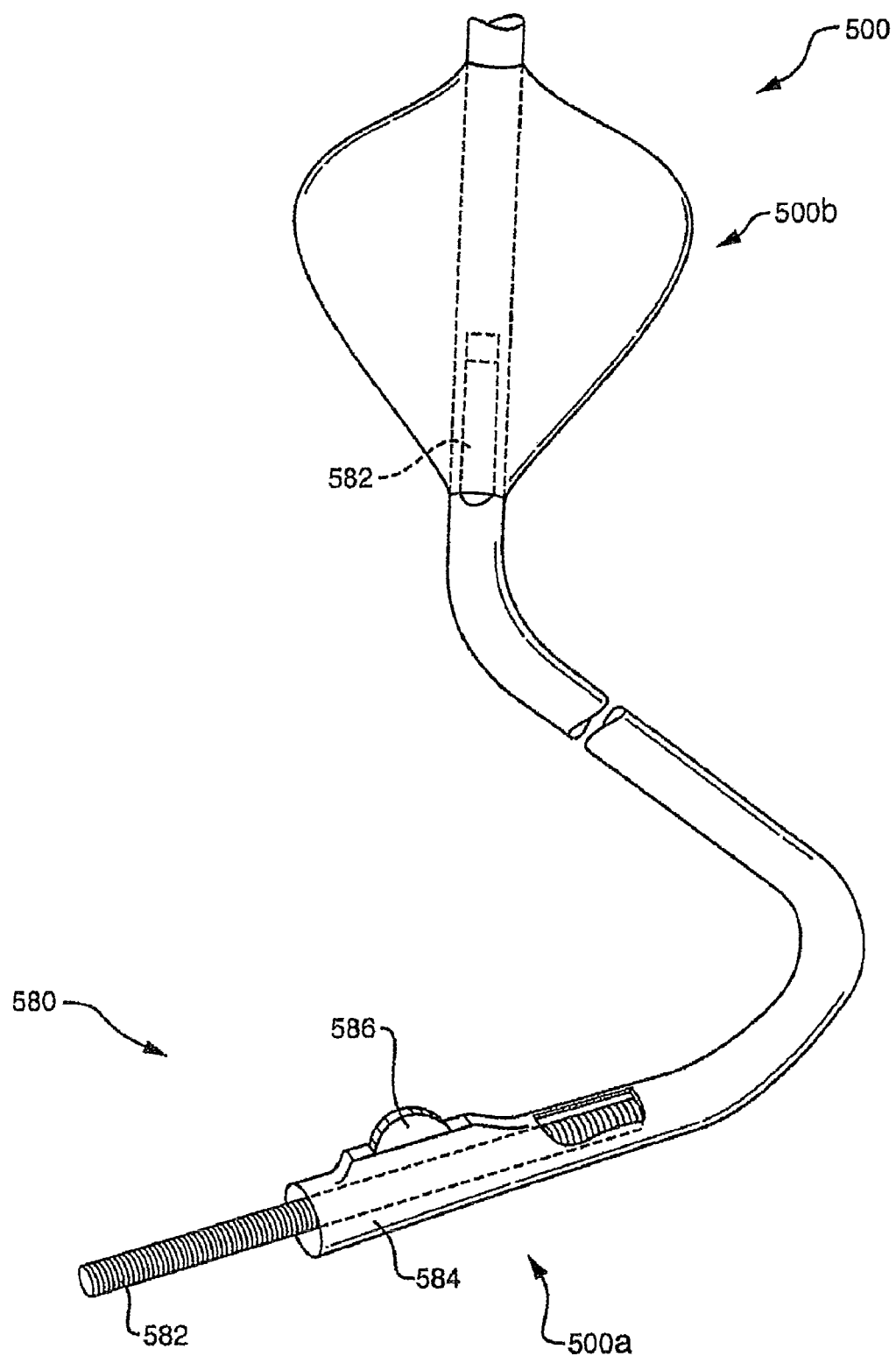
FIG. 11 is a schematic illustration of a mechanism for positioning the radiant energy emitter at a selected location relative to the target tissue region.

An ablation instrument 500 can also be used with a deflectable sheath catheter. While the ablation instrument 500 can have a variety of configurations, the ablation instrument 500 has proximal and distal ends 500a, 500b and is adapted to pass through an inner lumen of the deflectable catheter into position in proximity to a target treatment site. As shown in FIG. 11, the ablation instrument 500 can include a radiant energy emitter. While the radiant energy emitter can have a variety of configurations, in an exemplary embodiment it includes an elongate body 589 as well as a translatory mechanism 580 for controlling its movement within an ablation instrument 500 following its delivery through the deflectable sheath catheter. The translatory mechanism 580 can have a variety of configurations, and as shown it can be incorporated into a handle 584 in the proximal end 500a of the ablation instrument 500. Moreover, the translatory mechanism 580 can have a variety of control mechanisms, such as either an automated or manual control mechanism, however in an exemplary embodiment translatory mechanism 580 has a thumb wheel 586 that can engage the elongate body 582 of the radiant energy emitter 540 to control advancement and retraction of the emitter.

One skilled in the art will appreciate that catheter disclosed herein can incorporate a variety of other designs and features in addition to those features disclosed above. For example, similar to U.S. Pat. No. 6,522,933 entitled "Steerable Catheter with a Control Handle having a Pulley Mechanism," which is herein incorporated by reference, the catheter can have a control handle having a piston slidably mounted in the handle housing and a pulley fixedly attached, either directly or indirectly, to the handle housing at a location proximal to the proximal end of the piston by first and second puller wires. The handle portion can also be shaped as a pistol grip such that the handle is under a spring-loaded force to maintain a backpressure on the handle similar to that as disclosed in U.S. Pat. No. 6,679,873 entitled "Method for using a Steerable Catheter Device," which is herein incorporated by reference.

Additionally, the catheter can have a distal tip with a spring element biased to return the tip to a substantially straight position similar to that seen in U.S. Pat. No. 6,702,780 entitled "Steering Configuration for Catheter with Rigid Distal Device," herein incorporated by reference. The catheter can also include compression coils or flat flexible wires such that when a user engages a steering assembly, a distal end of the tubular body can be selectively bent in a first direction or in a second direction depending upon which coil or wire is actively displaced as seen in U.S. Pat. No. 6,579,278 entitled "Bi-Directional Steerable Catheter with Asymmetric Fulcrum," herein incorporated by reference, or a deflection mechanism similar to that as disclosed in U.S. Pat. No. 6,251,092 entitled "Deflectable Guiding Catheter," also herein incorporated by reference.

Moreover, the catheters of the present invention can be constructed with any biocompatible materials known in the art such for example, silastic, polyethylene, Teflon, polyurethanes, etc. Moreover, the lumen formed therein can be lined with a stiffening element.

Figure 12:
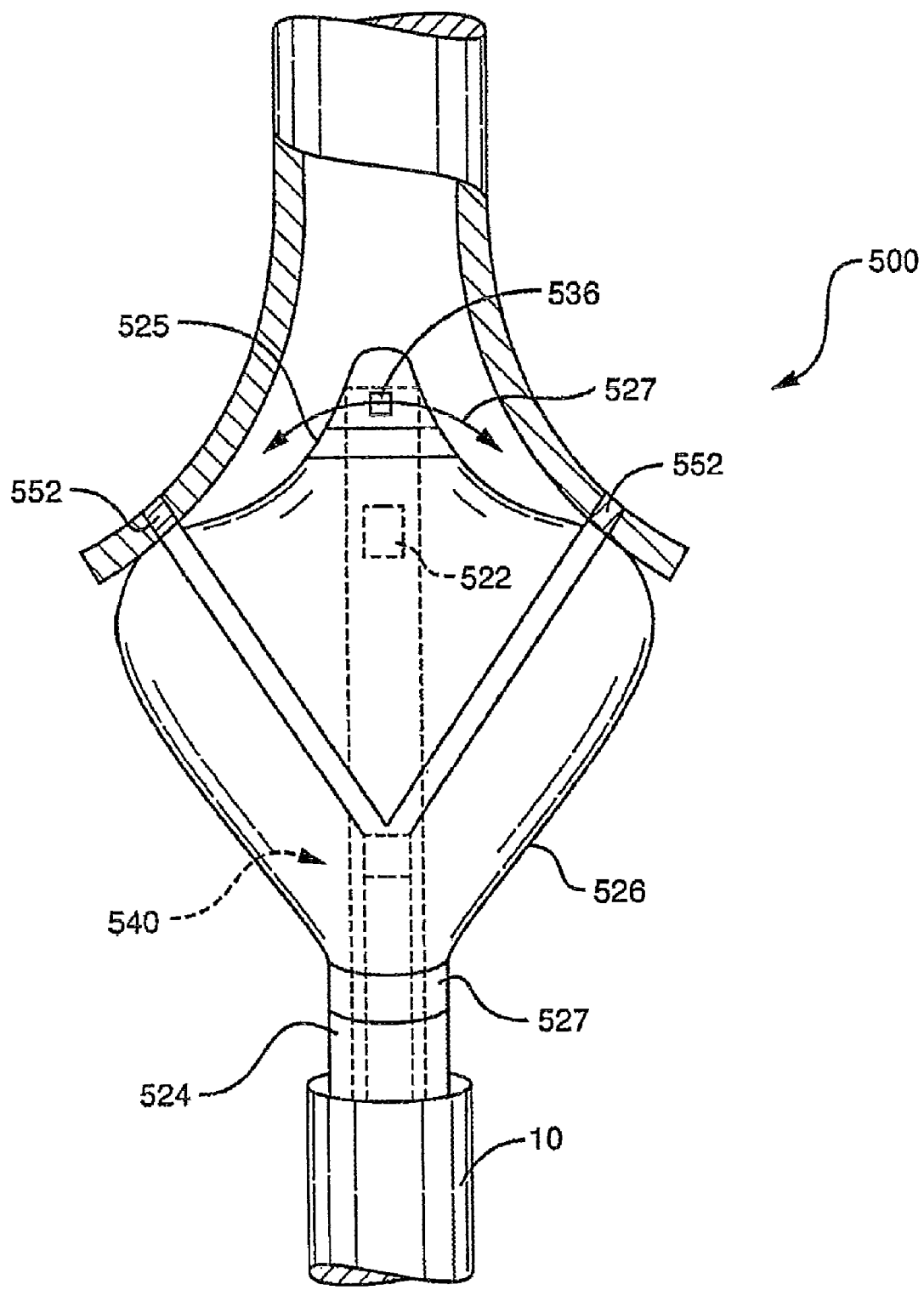
FIG. 12 is a schematic, cross-sectional view of a coaxial catheter ablation instrument according to the invention.

FIGS. 12 to 22 illustrate methods for performing ablative surgery using the catheter disclosed above. FIG. 12 is a schematic illustration of a method of performing ablative surgery with radiant energy according to the invention. As shown, after the sheath catheter 10 is introduced into a heart and positioned in front of a pulmonary vein 516, the ablation instrument 500 is slid through the sheath catheter 10 to the target tissue site.

Ablation instrument 500 is similar to the ablation instrument discussed above with respect to FIG. 11, however also includes a projection balloon structure 526 attached to catheter 10 and at least one internal fluid passageway (not shown)

for inflation of the balloon 526. While the balloon 526 can be attached to the catheter 10 in a variety of ways, in an exemplary embodiment the balloon 526 is sealed to the body of the catheter 524 by distal seal 525 and proximal seal 527, such that the introduction of an inflation fluid into the balloon 526 can inflate the balloon. One having skill in the art will appreciate that projection balloon 526 can be inflated to define a projection pathway for radiant energy ablation of cardiac tissue.

While the projection balloon 526 can have a variety of configurations, the projection balloon 526 can be preshaped to form parabolic like or various other shapes to assist in seating the instrument at the mouth of a pulmonary vein or otherwise engaging the vein ostium or other anatomically defined regions of the heart. While such shapes can be formed in a variety of ways, in an exemplary embodiment they are formed by shaping and melting a TEFLON® film in a preshaped mold to the desired form. Alternatively, the projection balloons 526 can be made from a thin wall of polyethylene teraphthalate (PET) membranes. While the membranes can have a variety of thicknesses, in an exemplary embodiment, the membranes have a thickness of about 5-50 micrometers.

As noted above, following inflation, the projection balloon 526 can be filled with a radiation-transmissive fluid 529 so that radiant energy from an energy emitter can be efficiently passed through the instrument to a target region 552 of cardiac tissue. The ablative fluid 529 in this context is any fluid that can serve as a conductor of the radiant energy, e.g., any physiologically compatible fluid, such as saline, or any other non-toxic aqueous fluid. The fluid 529 can also serve an irrigation function by displacing any blood within the path of the radiant energy, which could otherwise interfere with the radiant light energy transmission to the target region 552.

While the fluid 529 can enter the balloon 526 in a variety of ways, in an exemplary embodiment the fluid 529 can be released via one or more exit ports 536 to flow between the projection balloon 526 and the surrounding tissue, thereby filling any gaps where the balloon 526 does not contact the tissue. Moreover, the radiation transmissive fluid 529 can be continually released (e.g., between the balloon 526 and the target region 552) to ensure efficient transmission of the radiant energy when the instrument is deployed.

One skilled in the art will appreciate that the projection balloon 526 can not only contact the target tissue in order to ensure radiant energy transmission, but the projection balloon 526 can also serve to clear a volume of blood away from the path of the energy emitter.

Another method disclosed herein is based on the discovery that infrared radiation is particularly useful in forming photoablative lesions. Thus, an ablative instrument can emit radiation at a wavelength in a range from about 800 nm to about 1000 nm, and preferably emit at a wavelength in a range of about 915 nm to about 980 nm such that a lesion is formed. One skilled in the art will appreciate that the emission of radiation at wavelengths in the range of about 915 nm or 980 nm allows for the optimal absorption of the infrared radiation by cardiac tissue.

In a further aspect of the invention, the ablation instrument can perform photoablation, e.g., employing tissue-penetrating radiant energy to create the electrical conduction block. It has been discovered that radiant energy, e.g., projected electromagnetic radiation or ultrasound, can create lesions in less time and with less risk of the adverse types of surface tissue destruction commonly associated with prior art approaches. One skilled in the art will appreciate that unlike instruments that rely on thermal conduction or resistive heating, controlled penetrating radiant energy can be used to simultaneously deposit energy throughout the full thickness of a target tissue, such as a heart wall, even when the heart is filled with blood. Moreover, radiant energy can also produce better-defined and more uniform lesions.

In addition to infrared light-based ablation devices, other forms of radiant energy can also be useful including, but not limited to, other wavelengths of light, ultrasound, hypersound, radio frequency radiation, microwave radiation, x-rays, and gamma-rays. Moreover, contact ablation mechanisms, such as the application of heat by conductive or convective means, the application of cryogenic treatments, and/or the use ablative chemical or thermal fluids (either gaseous or liquid) can also be used to form a lesion.

Figure 13A:
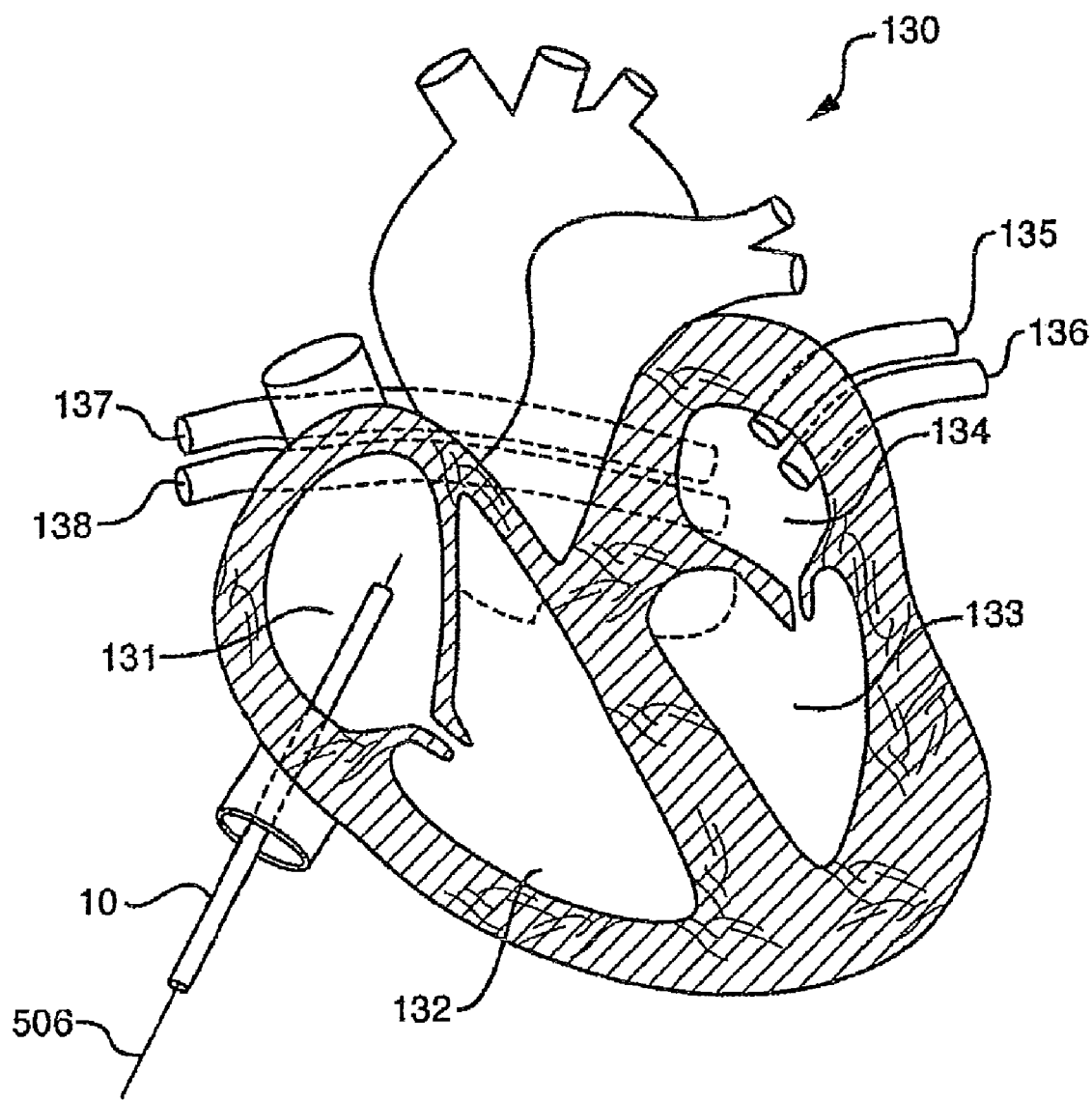
FIG. 13A is a schematic view of an embodiment of the present invention showing a deflectable sheath catheter accessing a human heart.

FIG. 13A illustrates an alternative method of cardiac access as disclosed herein. As shown, the human heart 130 has a right atrium 131, a right ventricle 132, a left ventricle 133 and a left atrium 134. Left pulmonary veins 135, 136 and right pulmonary veins 137, 138 drain into the left atrium, as shown schematically. The method can include positioning a guide wire 506 in the right atrium 131. The deflectable sheath catheter 10 is then passed over the guide wire, and the distal end of the deflectable sheath catheter 10 is deflected such that the tip of the catheter 10 provides access to the pulmonary veins in the left atrium of the heart 135, 136.

Figure 13B:
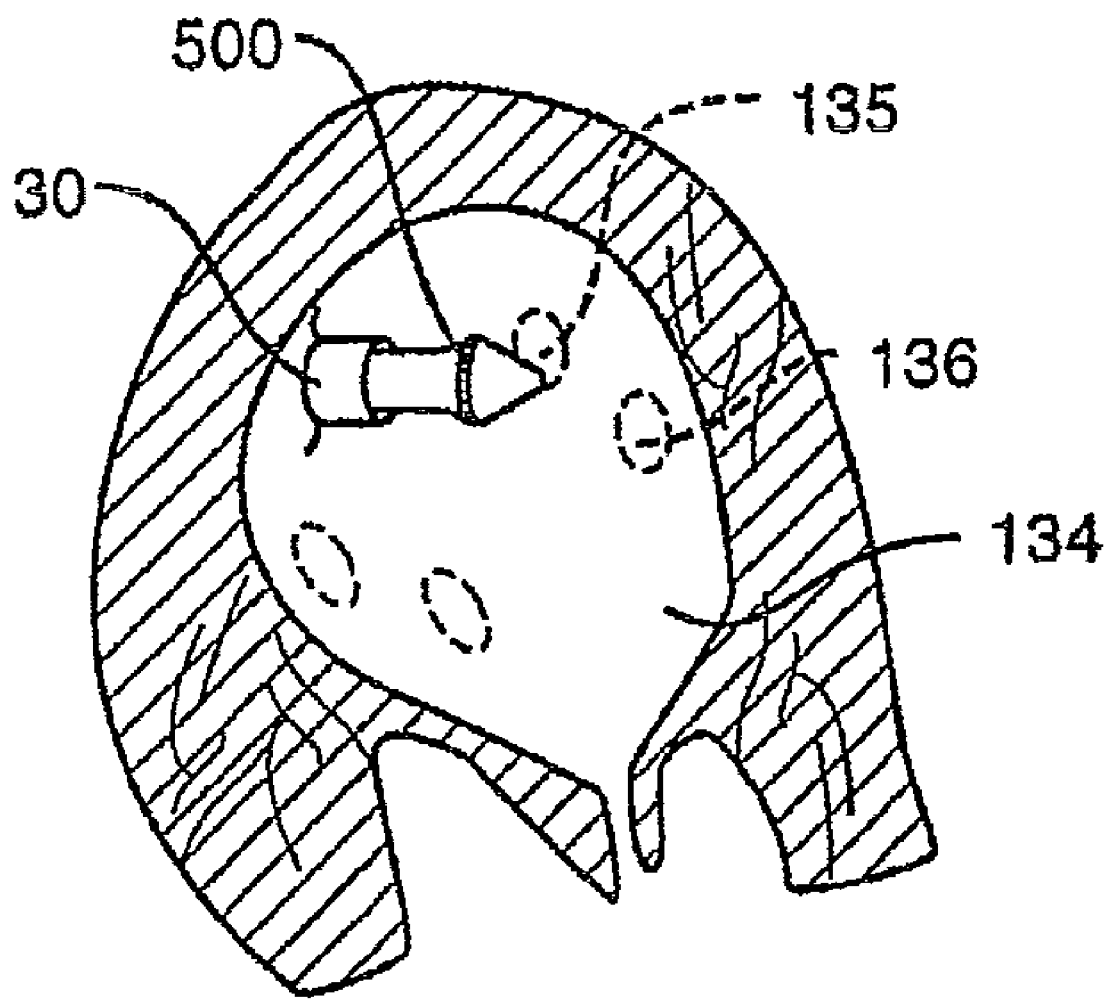
FIG. 13B is a schematic view of the left atrium of a human heart in which the deflectable sheath of the present invention is used to access the ostium of a left pulmonary vein.
Figure 13C:
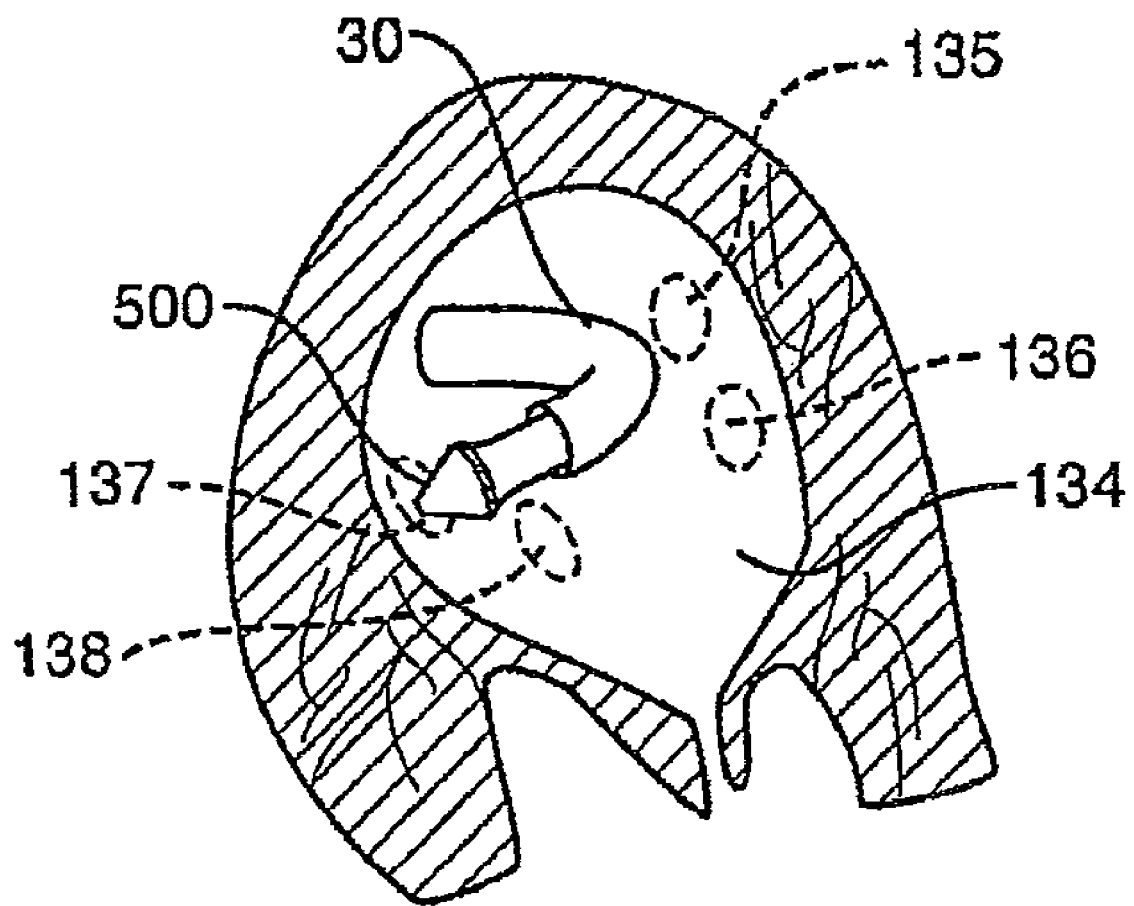
FIG. 13C is a schematic view of the left atrium of a human heart in which the deflectable sheath of the present invention is used to access the ostium of a right pulmonary vein.

Once in the pulmonary veins 135, 136, as shown in FIG. 13B, the deflectable tip section of the catheter 10 can be locked in a bent position pointing at the ostium/atrium of a left pulmonary vein 135 or the surrounding endomyocardium such that an ablation instrument 500 can be introduced into the target region and the target region ultimately ablated. Alternatively, following introduction into the target region the deflectable catheter 10 can be unlocked and repositioned as shown in FIG. 13C. One skilled in the art will appreciate that the deflectable sheath catheter 10 disclosed herein allows an operator to deflect the catheter 10 at least 180° so that the deflectable tip section of the catheter 10 can "loop over" or arch over the roof of the atrium in order to point the distal section of the catheter 10 at the ostium of the right pulmonary veins 137, 138.

Not only can the catheter 10 deliver ablation energy, but it can also deliver treatment fluid, such as saline, or a medical instrument, such as an ablation instrument, to each of the four pulmonary veins in order to access, align, and aid in the treatment of atrial fibrillation by isolation (ablation) of the pulmonary veins. One skilled in the art will also appreciate that the deflectable catheter 10 also facilitates contact with the pulmonary vein ostia by allowing the clinician to apply axial force to an ostium with the ablation instrument, as this axial force typically cannot be applied with a deflectable ablation instrument alone.

Figure 14:
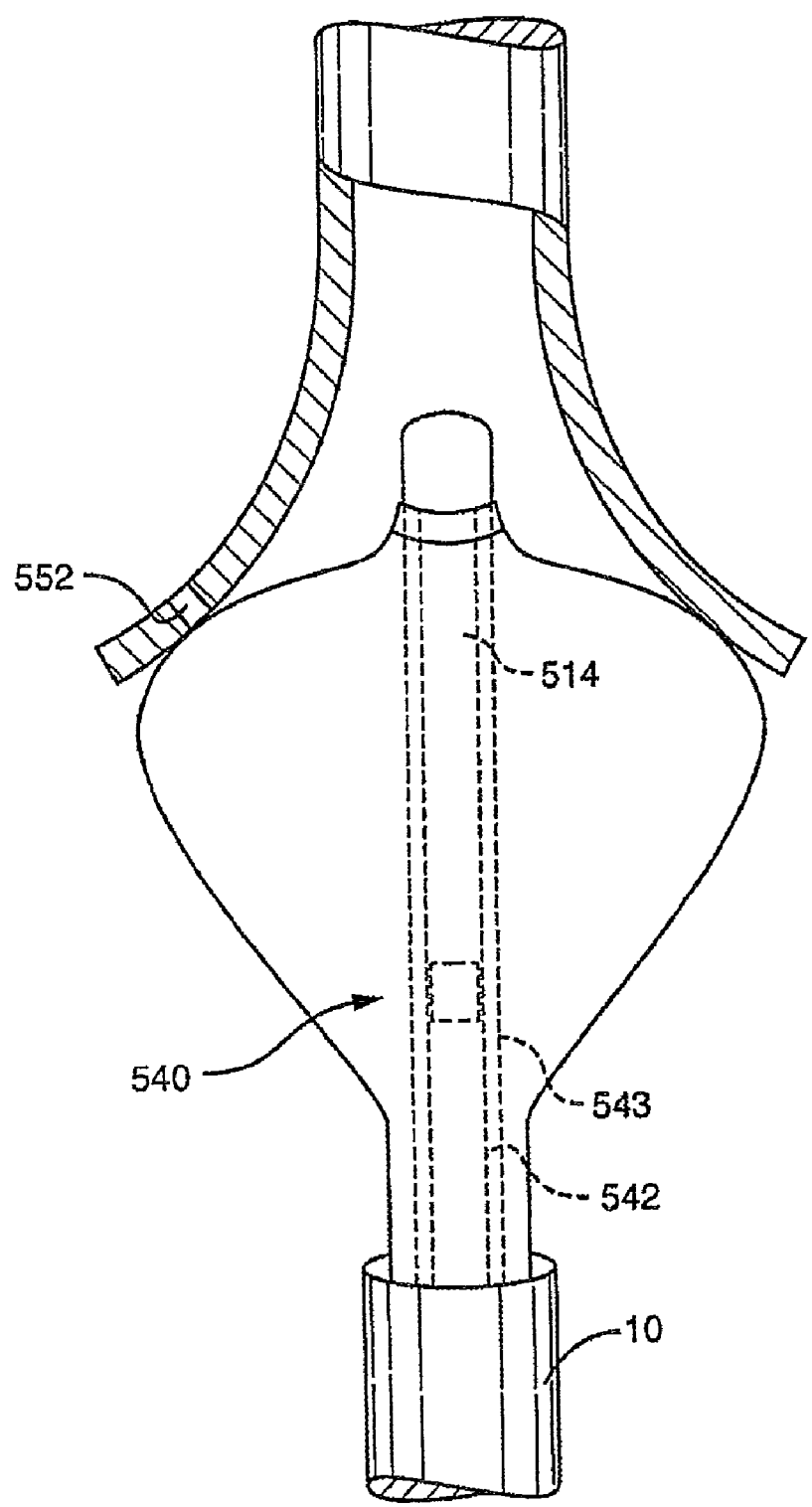
FIG. 14 is a schematic illustration of a further step in performing ablative surgery according to the invention, in which the guide wire and dilator are removed and replaced by a radiant energy emitter located remote from the lesion site but in a position that permits projection of radiant energy onto a target region of the heart.

As shown in FIG. 14, another embodiment of a method for ablating cardiac tissue includes positioning a guide wire in proximity to a target region of cardiac tissue 552 and coupling a deflectable sheath catheter 10 having at least one lumen 514 to the positioned guide wire via the lumen 514, such that the sheath catheter 10 can be passed over the guide wire to a target region of cardiac tissue 552. The sheath catheter 10 can further include a concentric dilator or stiffening element that serves as a lining within the catheter 10, and in such applications the method further comprises passage of the catheter 10 and dilator assembly over the guide wire. Next, the deflectable sheath catheter 10 (and the optional stiffening element) can be passed over the guidewire into a position within the heart and used to create a transeptal puncture into the left atrium. The guide wire can be removed before or after the septum is punctured. Once the sheath catheter 10 is positioned in proximity to the target site (e.g., the ostium of a pulmonary vein) the dilator can be removed and replaced with an ablation instrument slidably movable within a lumen of the deflectable sheath catheter 10 such that it can be disposed at the desired location (such as target tissue 552).

While the energy emitter can vary depending upon the procedure, in the illustrated embodiment, the energy emitter 540 is a radiant energy emitter having at least one optical fiber 542 coupled to a distal, light projecting, optical element 543, which cooperate to project ablative light energy through the instrument to the target site 552. In one preferred embodiment, the optical element 543 is a lens element capable of projecting an annular (ring-shaped) beam of radiation, as described in more detail in commonly owned U.S. Pat. No. 6,423,055 issued Jul. 22, 2002, herein incorporated by reference. The method further includes activating the ablation instrument in proximity to the target tissue region to ablate tissue and form a conduction block.

Figure 15:
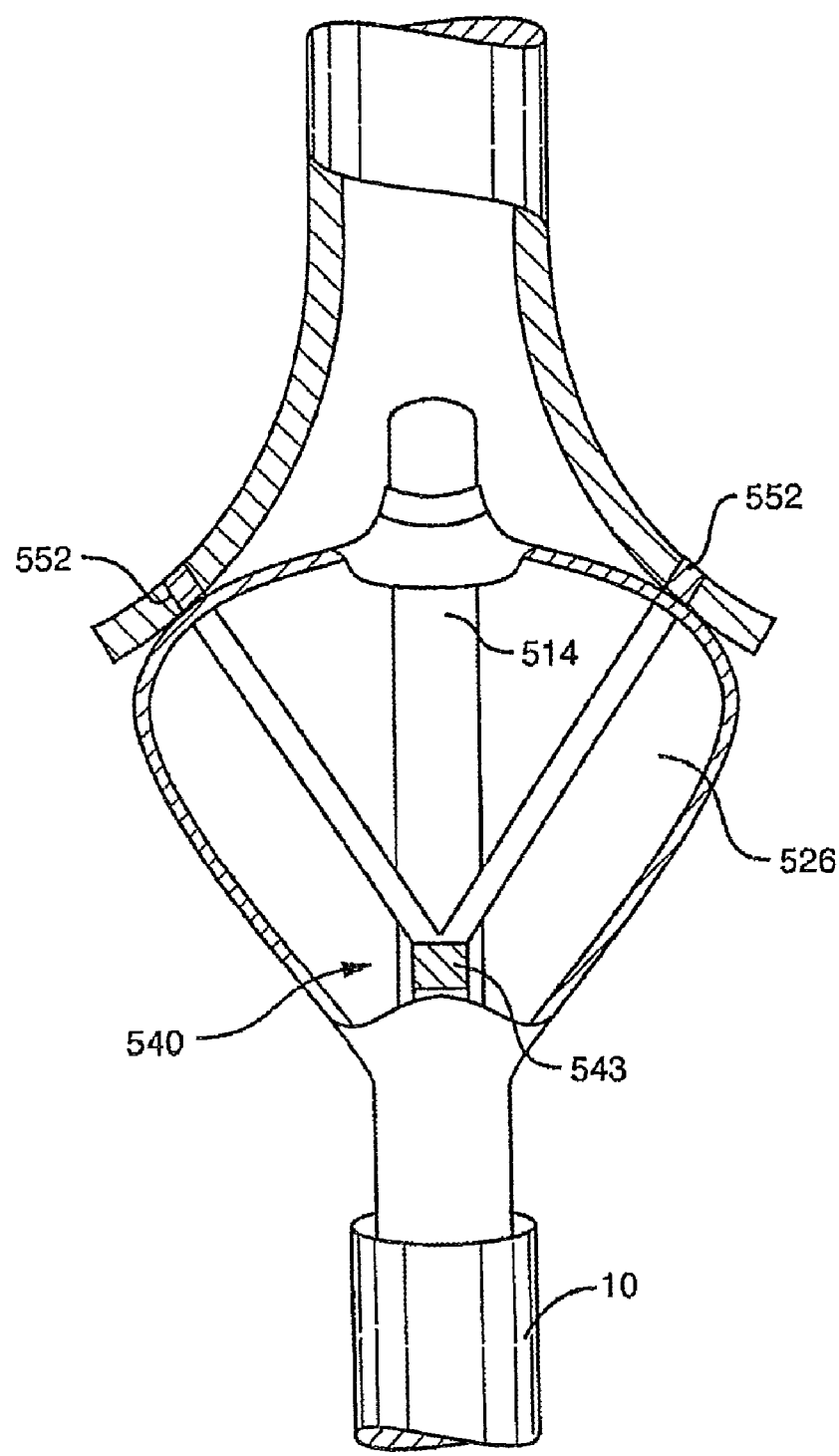
FIG. 15 is a schematic illustration of a step in performing ablative surgery according to the invention, in which a radiant energy emitter is positioned to form a lesion at a defined location.
Figure 16:
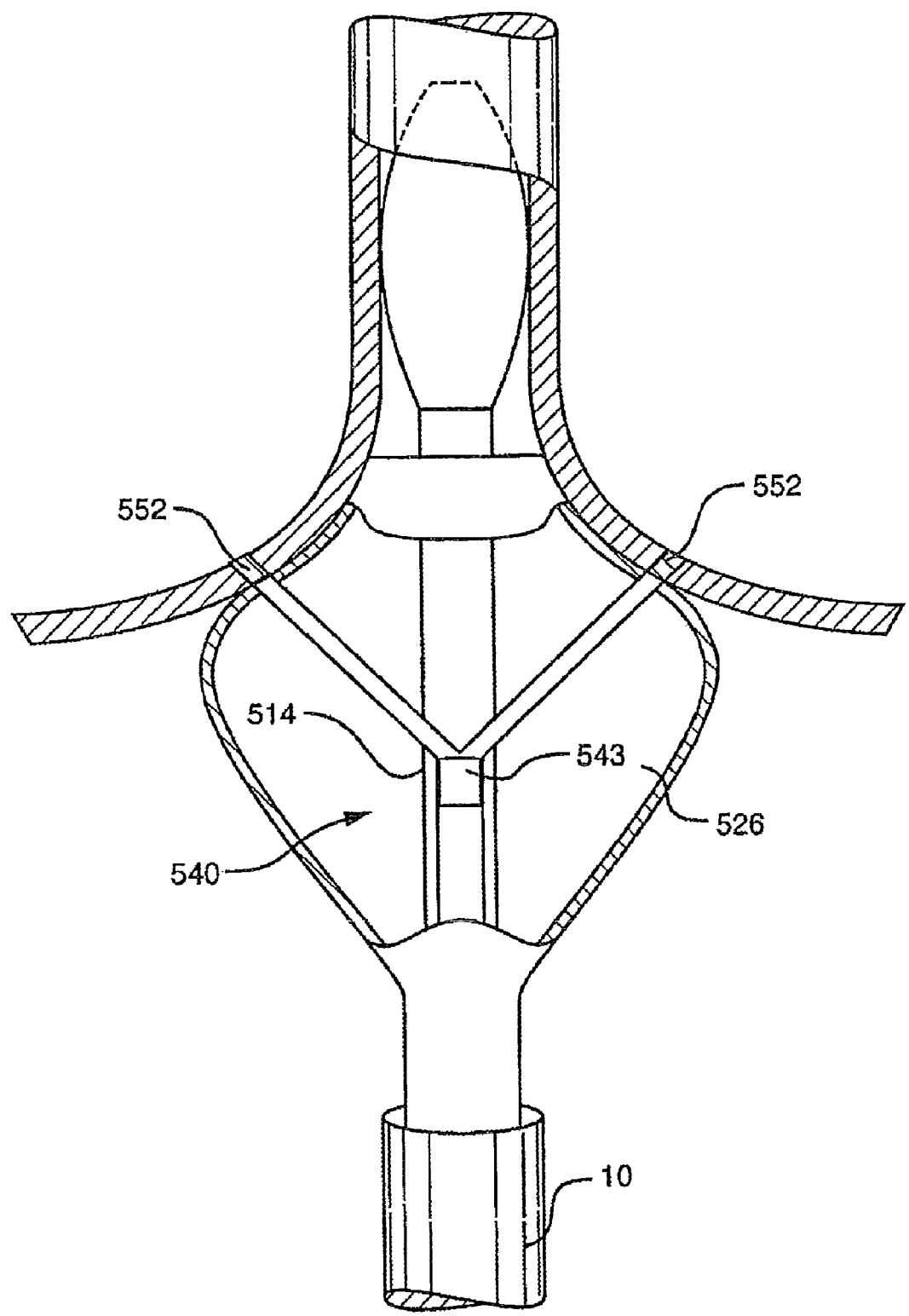
FIG. 16 is a schematic illustration of an alternative step in performing ablative surgery according to the invention, in which the radiant energy emitter is positioned to form a lesion at a different defined location.

FIGS. 15 and 16 illustrate another method disclosed herein wherein a surgeon can select the location of a lesion independent of the instrument design. The method is similar to that as discussed with respect to FIG. 14, however, because the radiant energy emitter 540 does not require contact with a target tissue region 552 and is, in fact, decoupled from the rest of the ablation instrument, the present invention permits the clinician to select a desired target region by simply moving the emitter 540 within the lumen 514 of the deflectable sheath catheter 10. As shown in FIG. 15, the radiant energy emitter 540 can be positioned to form a wide circumferential lesion (when the shape of the pulmonary vein ostium warrants such a lesion) by positioning the radiant energy emitter 540 at the rear of the projection balloon 526 at a distance from the target tissue. Alternatively, positioning the radiant energy emitter 540 closer to the front of the project balloon 526, as shown in FIG. 16, can form a smaller diameter lesion. One skilled in the art will appreciate that a smaller lesion can be used when the geometry of the vein ostium presents a more gradual change in diameter, as shown. Moreover, it should be appreciated that it may be desirable to change the intensity of the emitted radiation depending upon the distance it must be projected; thus a more intense radiant energy beam may be desirable in the scheme illustrated in FIG. 15 versus that shown in FIG. 16.

Figure 17:
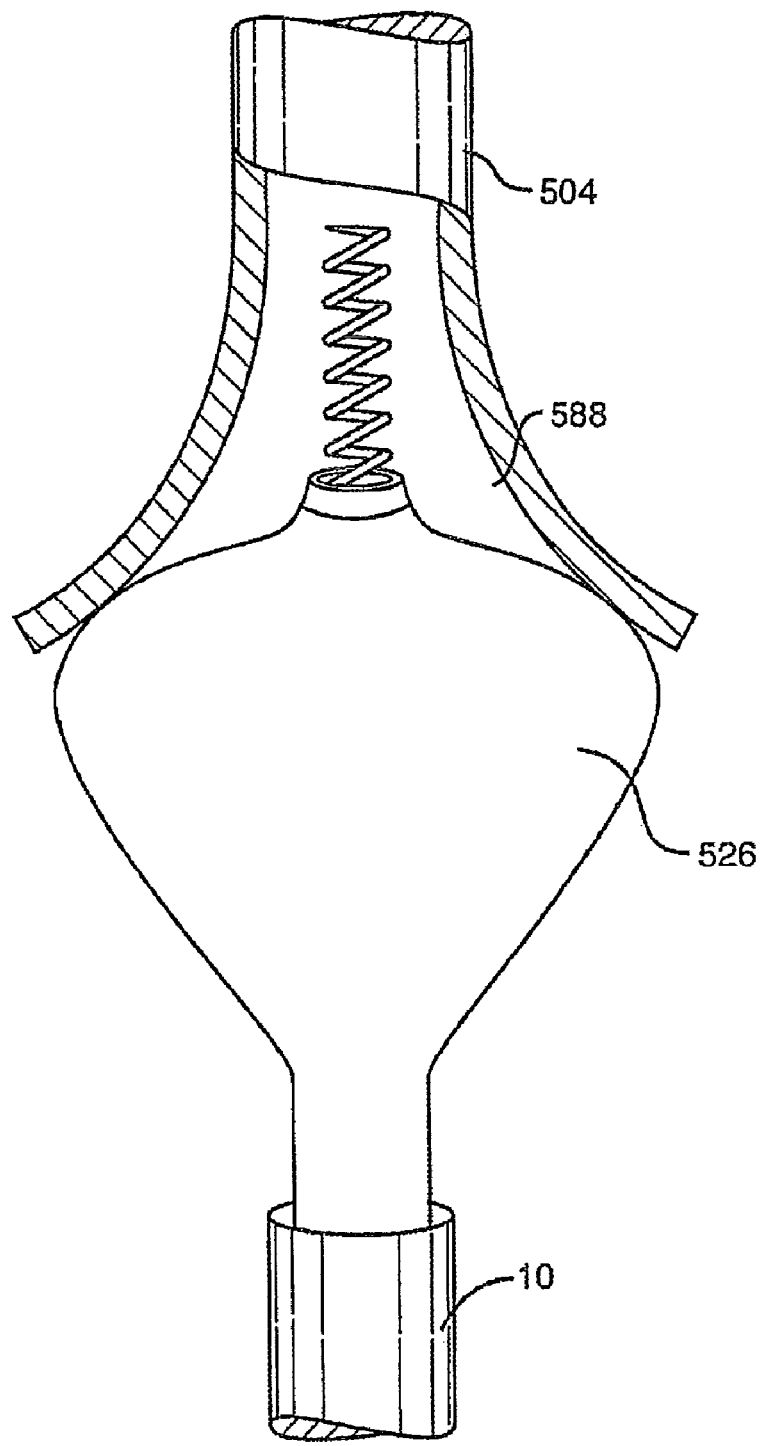
FIG. 17 is a schematic illustration of a further step in performing ablative surgery according to the invention, in which the ablation element is replaced by a mapping electrode.

In another embodiment, shown in FIG. 17, a mapping electrode catheter 588 can be passed through the ablation instrument, after the instrument has been delivered through the deflectable sheath catheter 10 and positioned within a pulmonary vein 504. Using the mapping electrode 588, an electrical pulse can be applied to determine whether the lesion formed by the radiant energy emitter (as described above) is sufficient to serve as a conduction block. Various techniques for verifying the formation of an electrical conduction block are known by those skilled in the art. In one simple approach, a coronary sinus catheter applies a voltage pulse, and the mapping catheter electrode 588 is touched to the inner wall of the pulmonary vein 504. If no signal (or a substantially attenuated signal) is detected, a conduction block can thereby be confirmed. It should also be appreciated that the mapping electrode 588 can, in some instances, be used even before the projection and/or anchor balloons 526 are removed.

Figure 18:
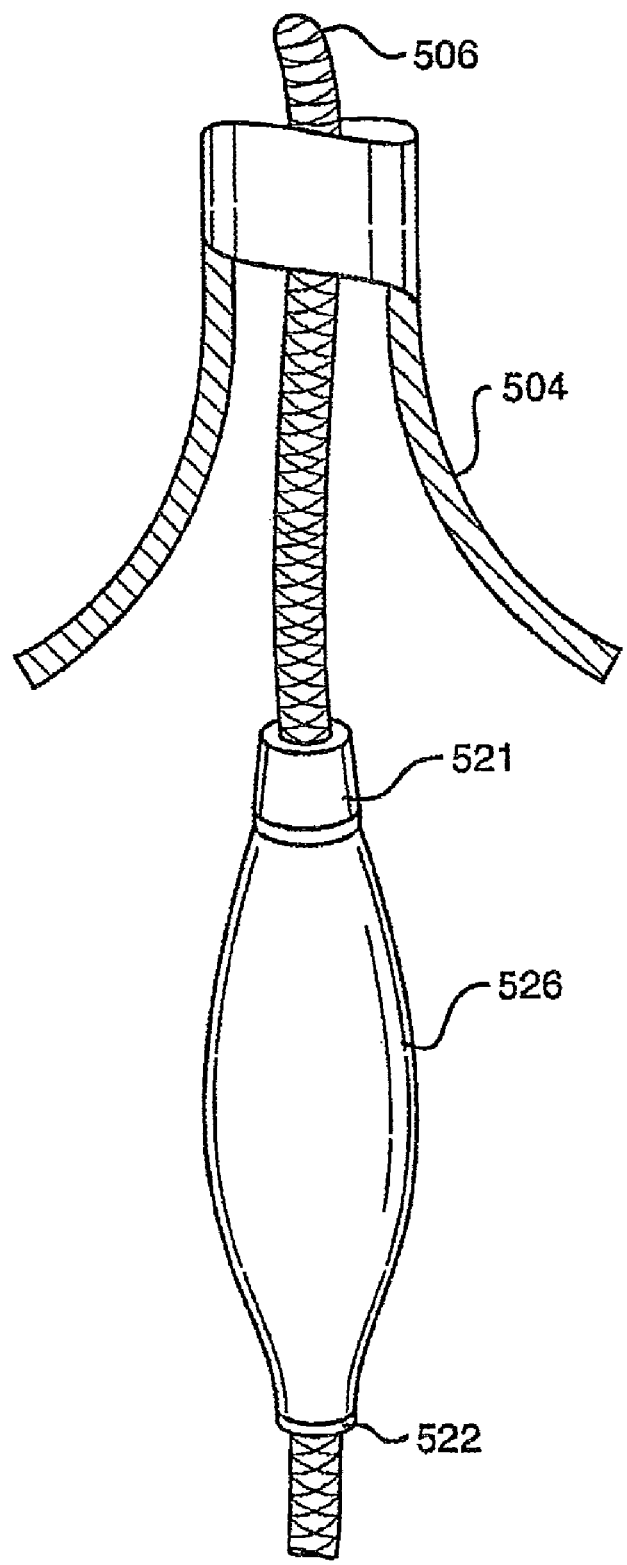
FIG. 18 is a schematic illustration of an alternative approach to ablative surgery with radiant energy according to the invention, in which an ablation instrument without an anchorage element is placed in a position proximal to a pulmonary vein via the deflectable sheath catheter.

Moreover, the methods described in FIGS. 12 to 17 can also include the use of an anchoring element, such as an anchoring balloon, to maintain the catheter the desired position of the catheter with respect to the target tissue. However, as shown in FIG. 18 ablative surgery with radiant energy according to the invention can be performed without the need for an anchoring balloon. As shown in FIG. 18, a guide wire 506 can be introduced into a heart and passed into the proximity of a pulmonary vein 504. The deflectable sheath catheter (with or without a stiffening liner or dilator element) can be passed over the guide wire 506 and into the heart. Following insertion into the heart, the deflectable sheath catheter can serve as a platform for the introduction of an ablation instrument. The ablation instrument can be a balloon catheter similar to projection balloon 526 discussed above having an elongate body with at least one internal fluid passageway (not shown) for inflation of the balloon 526, and which is sealed to the body of the catheter by distal seal 521 and proximal seal 522, such that the introduction of an inflation fluid into the balloon 526 can inflate the balloon 526. One skilled in the art can also appreciate that, even without the use of any type of anchoring element, the deflectable sheath catheter not only can point the ablation instrument in the proper direction but also permits the clinician to apply sufficient axial pressure to seal the balloon against the mouth of a pulmonary vein.

Figure 19:
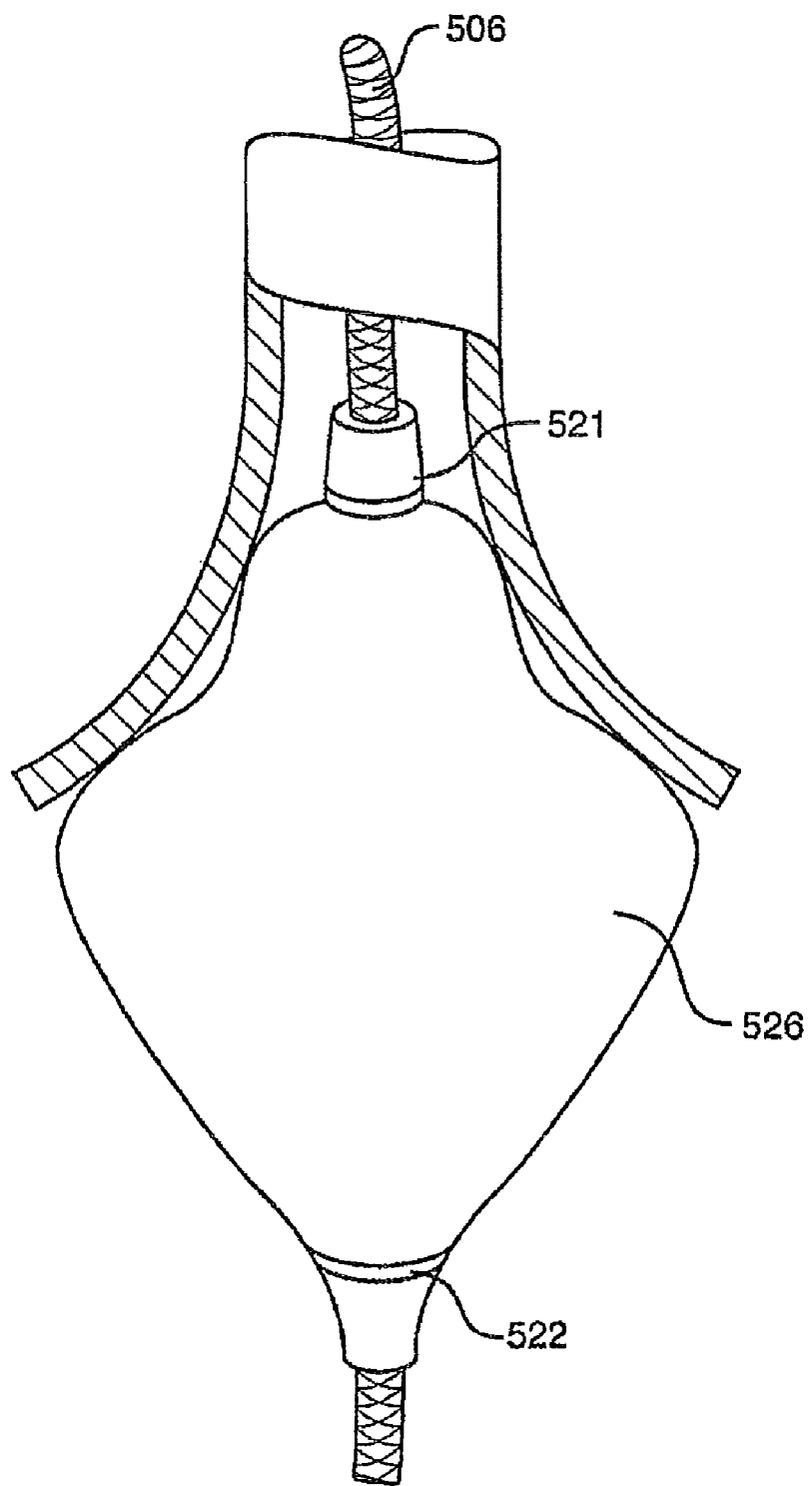
FIG. 19 is a schematic illustration of a further step in performing ablative surgery with the embodiment illustrated in FIG. 18, in which the ablation element is a radiant energy emitter and a projection balloon element is inflated to define a projection pathway for radiant energy ablation of cardiac tissue.

As noted above, following insertion, the projection balloon 526 can then be inflated to define a projection pathway for radiant energy ablation of cardiac tissue. As shown in FIG. 19, the expanded projection balloon 526 defines a staging through which radiant energy can be projected in accordance with the invention. In one preferred embodiment, and similar to that discussed in FIG. 12, the projection balloon 526 is filled with a radiation-transmissive fluid so that radiant energy from an energy emitter can efficiently pass through the instrument to a target region of cardiac tissue.

Figure 20:
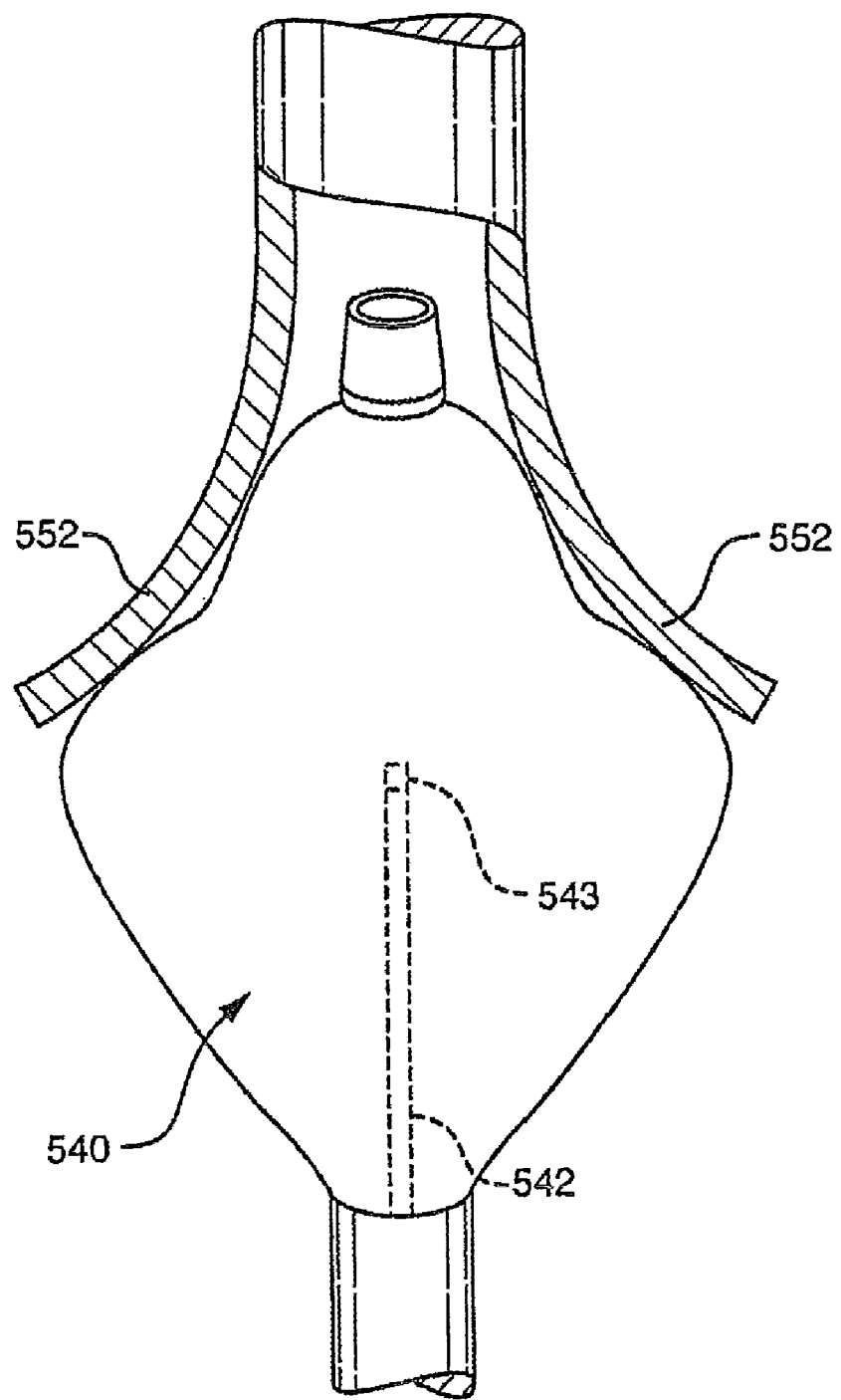
FIG. 20 is a schematic illustration of a further step in performing ablative surgery with the embodiment illustrated in FIG. 19, in which the radiant energy emitter is positioned within the projection balloon to deliver radiant energy onto a target region of the heart.

FIG. 20 is a schematic illustration of a further step in performing ablative surgery with the device of FIGS. 18 and 19, in which the guide wire and dilator are removed from the deflectable sheath catheter and replaced by an ablation instrument 540 located remote from the desired lesion site 552 (but still in a position that permits projection of radiant energy onto a target region of the heart). In the illustrated embodiment, the radiant energy emitter 540 includes at least one optical fiber 542 coupled to a distal light projector, such as optical element 543, which cooperate to project ablative light energy through the instrument induce photocoagulation of cardiac tissue within the target region. In one preferred embodiment, optical element 543 is again a lens element capable of projecting an annular (ring-shaped) beam of radiation, as described in more detail in commonly owned U.S. Pat. No. 6,423,055 issued Jul. 22, 2002, herein incorporated by reference. Alternatively, as noted above, the radiant energy emitter can be an ultrasound or microwave energy source.

Endoscopic guidance systems can further be used to position any movable point source of ablative energy, e.g., a rotating contact or radiant ablation element in lieu of a slidably positionable source or together therewith, such that the desired path can be visualized and followed by the ablation element. Most generally, endoscopic guidance systems can be used together with various fluoroscopic or other imaging techniques to location and position any one of the various instruments necessary for cardiac ablation.

The ability to position the energy emitter, especially when radiant light is employed as the ablation modality, also permits endoscopic aiming of the energy. For example, an aiming light beam can be transmitted via the catheter to the target site such that the physician can visualize where the energy will be delivered. Thus, endoscopic guidance permits the user to see where energy will be projected at various locations of the energy emitter. For example, if the instrument is designed to project light in an annular ring around the ostium of a pulmonary vein, the aiming beam can be projected down the same optical delivery path as would the radiant energy. If the "aiming ring" is projected onto a region of the atrium where a clear transmission pathway is seen, there is continuous contact (or the desired lesion path is otherwise cleared of blood), and the physician can begin the procedure. If, on the other hand, a clear transmission pathway is not seen at a particular location of the ablation element, then the ablation element can be moved until a clear lesion pathway is found. Although this "aiming" feature of the invention has been described in connection with radiant light energy sources, it should be clear that "aiming" can be used advantageously with any radiant energy source and, in fact, it can also assist in the placement of fixed or contact-based ablation elements. Most generally, endoscope-guidance can be combined with an aiming beam in any cardiac ablation system to improve positioning and predetermination of successful lesion formation.

Figure 21:
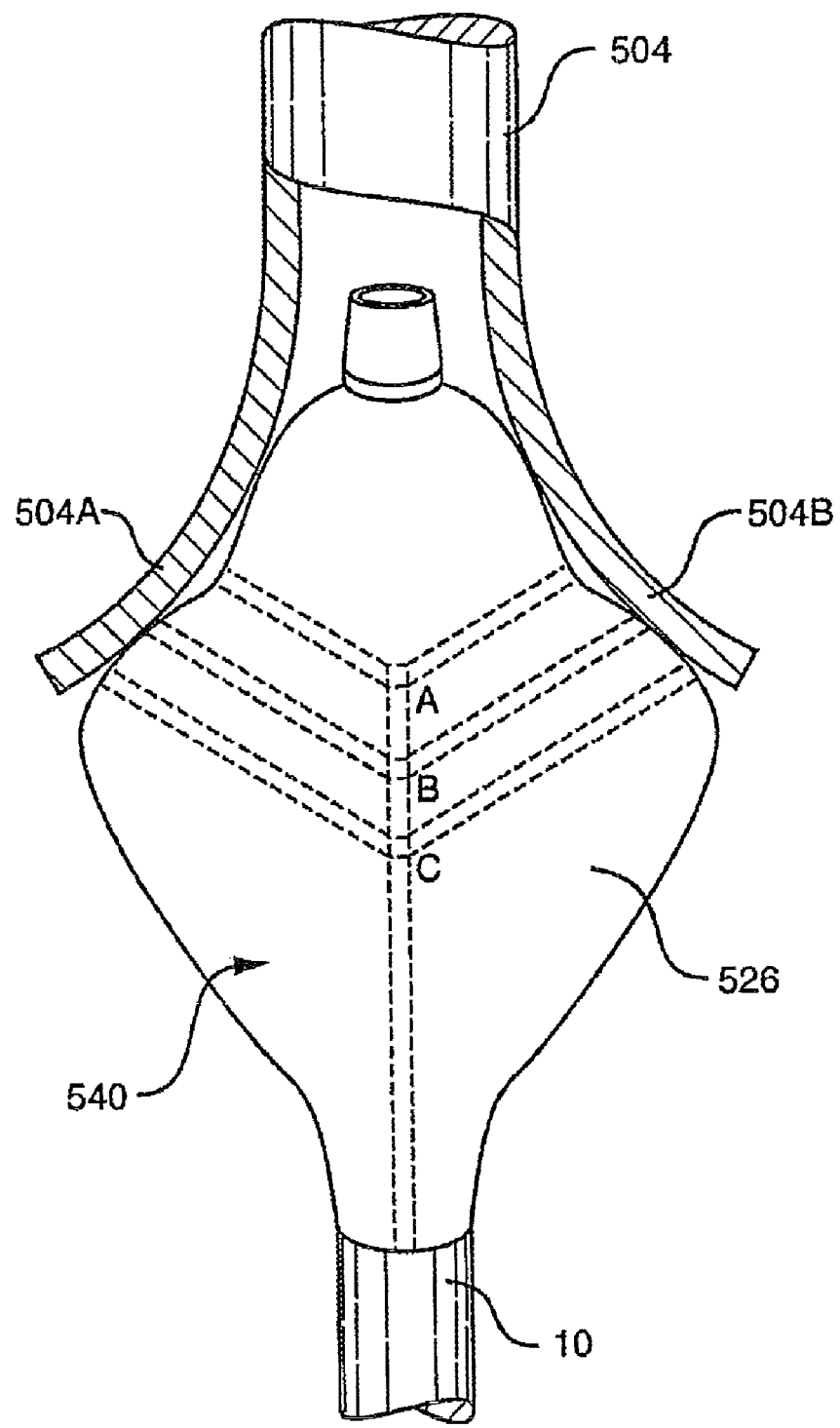
FIG. 21 is a schematic illustration of an instrument according to the invention in which an asymmetric vein mouth is encountered, and further showing how the position of the radiant energy emitter can be adjusted to sense contact and select a location.
Figure 22:
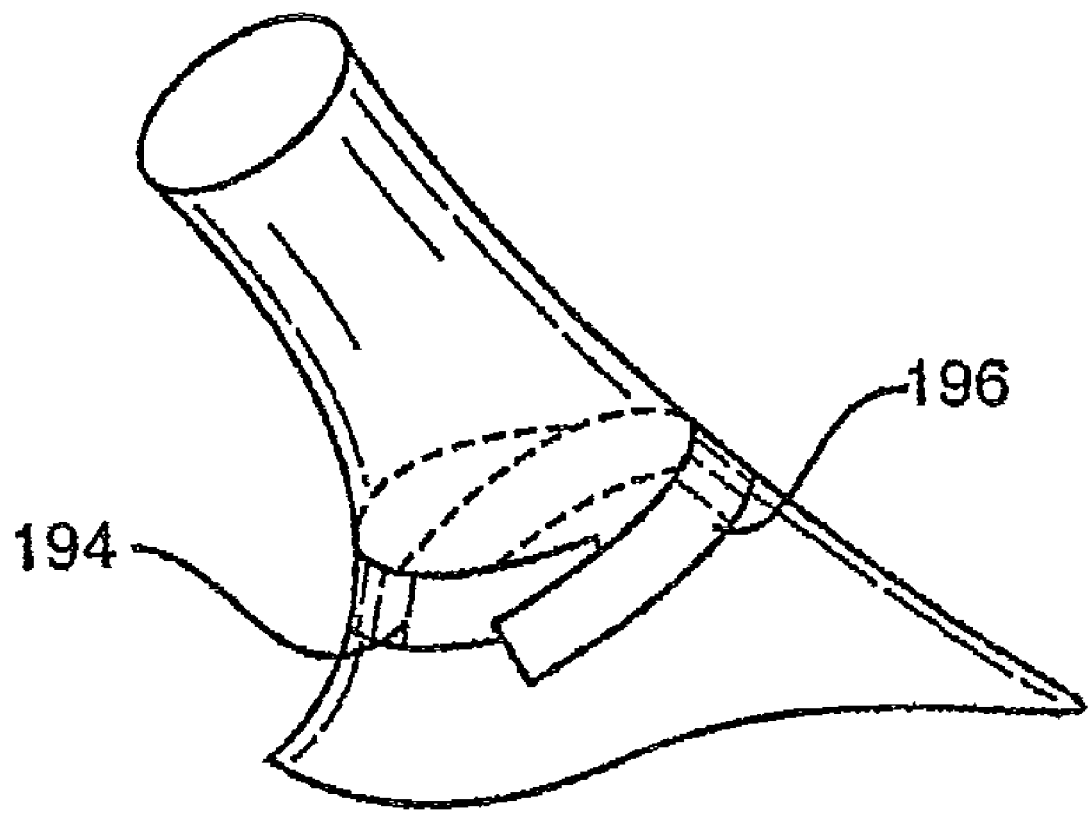
FIG. 22 illustrates how a continuous, vein-encircling lesion can be formed by two partially-encircling lesions.

FIGS. 21 and 22 further illustrate the unique utility of the multi-positionable, radiant energy ablation devices of the present invention in treating the complex cardiac geometries that are often encountered. As shown, the mouths of pulmonary veins (such as pulmonary vein 504) typically do not present simple, funnel-shaped, or regular conical surfaces. Instead, one side of the ostium 504B can present a gentle sloping surface, while another side 504A presents a sharper bend. Because the position of the heating band of the prior art devices is fixed, it does not fully contact the target tissue and a lesion that is in the form of an arc, or incompletely formed ring-type, will result. Such a lesion is typically insufficient to block conduction.

FIG. 21 illustrates how the slidably positionable energy emitters of the present invention can be used to avoid this problem. Three potential positions of the emitter 540 are shown in the figure (labeled as "A", "B" and "C"). As shown, positions A and C may not result in optimal lesions because of gaps between the balloon 526 and the target tissue. Position B, on the other hand, is preferable because circumferential contact has been achieved. Thus, the independent positioning of the energy source relative to the balloon 526 allows the clinician to "dial" an appropriately ring size to meet the encountered geometry. (Although three discrete locations are shown in FIG. 21, it should be clear that emitter can be positioned in many more positions and that the location can be varied in either discrete intervals or continuously, if so desired.)

Moreover, in some instances the geometries of the pulmonary vein 504 (or the orientation of the projection balloon 526 relative to the ostium) may be such that no single annular lesion can form a continuous conduction block. Again, the present invention provides a mechanism for addressing this problem by adjustment of the location of the energy emitter to form two or more partially circumferential lesions. As shown in FIG. 22, the devices of the present invention can form a first lesion 194 and a second lesion 196, each in the form of an arc or partial ring. Because each lesion 194, 196 has a thickness (dependent largely by the amount of energy deposited into the tissue) the two lesions 194, 196 can axially combine, as shown, to form a continuous encircling or circumscribing lesion that blocks conduction.

Figure 23:
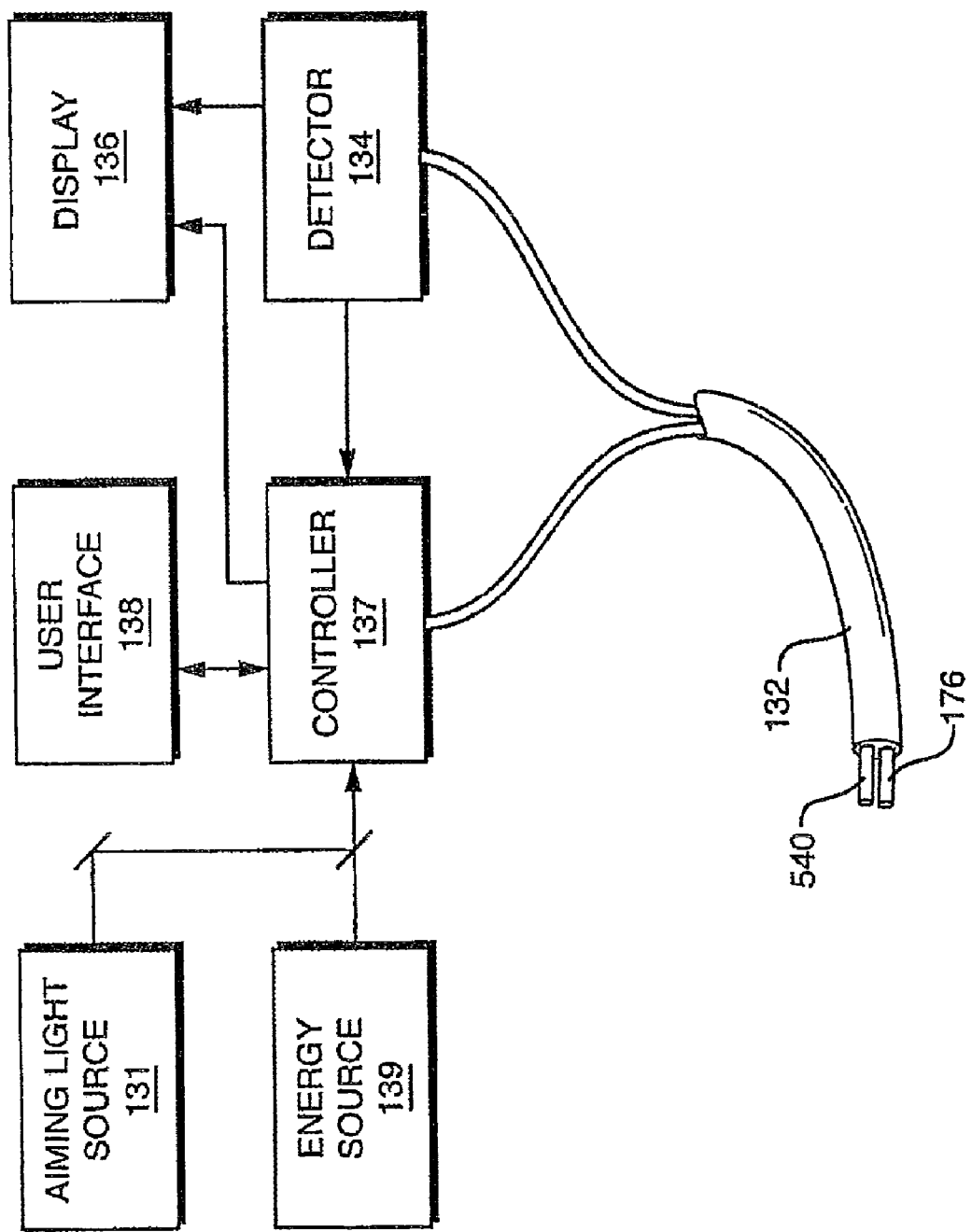
FIG. 23 is a schematic block diagram of the components of an endoscope-guided cardiac ablation system according to the invention.

FIG. 23 is a schematic block diagram showing an ablation instrument formed as an endoscope/ablator assembly 132 comprising endoscope 176 and ablation element 540 connected to an analyzer system. The analyzer system further includes a detector 134 for detecting reflected light (and for generating an image). The output of the detector 134 can be transmitted to a display 136 for clinician viewing. The display 136 can be a simple eyepiece, a monitor, or a heads-up projection onto glasses worn by members of the surgical team. The system can further include an energy source 139, a controller 137, and a user interface 138. In use, the endoscope 176 captures images which can be processed by the detector 134 and/or controller 137 to determine whether a suitable ablation path can be created. An aiming light source 131 can also be used visualize the location where energy will be delivery to the tissue. If a suitable ablation path is seen by the surgeon, the controller 137 can transmit radiant energy from the ablation element 139 to a target tissue site to effect ablation. Moreover, the controller 137 can provide simulated displays to the user, superimposing, for example, a predicted lesion pattern on the image acquired by the detector or superimposing dosimetry information based on the lesion location. The controller 137 can further include a memory for storing and displaying data, such as pre-procedure images, lesion predictions and/or actual outcomes, as well as a safety shutoff to the system in the event that a clear transmission pathway between the radiant energy source and the target tissue is lost during energy delivery.

Figure 24:
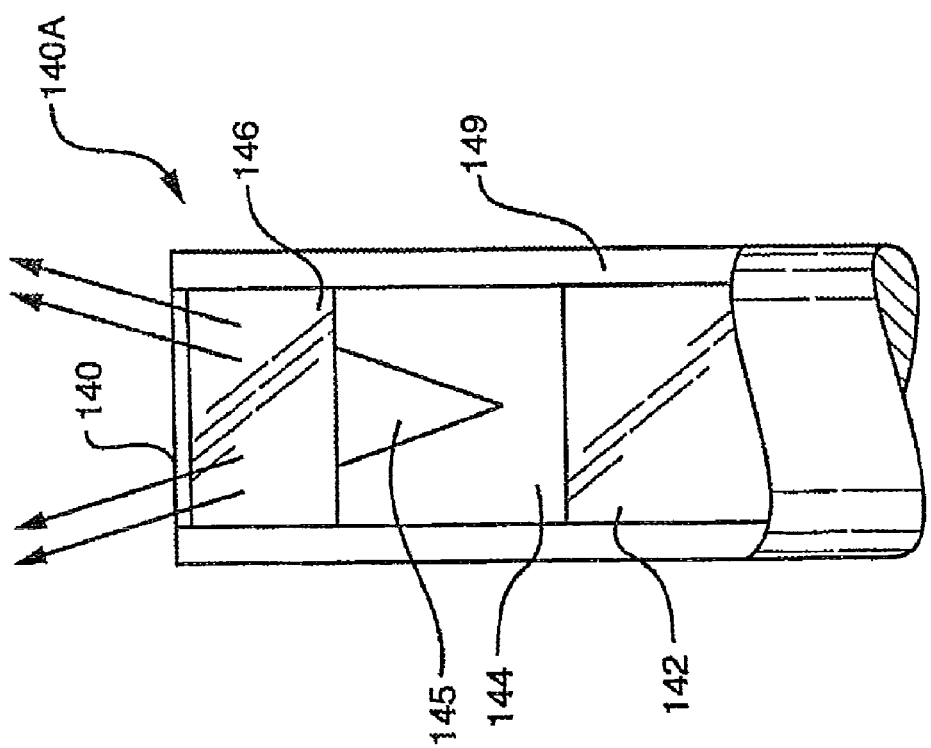
FIG. 24 is a schematic illustration of one embodiment of a radiant light energy emitter according to the invention.

FIG. 24 is a schematic illustration of one embodiment of a radiant energy emitter 140A according to the invention. While the energy emitter 140A can have a variety of configurations, as shown the energy emitter 140A can be a radiant energy emitter 140A that includes an optical fiber 142 in communication with an annulus-forming optical waveguide 144 having a concave interior boundary or surface 145. The waveguide 144 passes an annular beam of light to a graded intensity (GRIN) lens 146, which serves to collimate the beam, keeping the beam width the same, over the projected distance. Thus, the beam that exits from the distal window 148 of energy emitter 140 will expand (in diameter) over distance, but the energy will remain largely confined to a narrow annular band.

In one preferred embodiment, the radiant energy is electromagnetic radiation, e.g., coherent or laser light, and the energy emitter 140A projects an hollow cone of radiation that forms an annular exposure pattern upon impingement with a target surface. Generally, the angle of projection from the central axis of the optical fiber 142 or waveguide 144 will be between about 20° and 60° (for a total subtended angle of about 40° to about 120°). Moreover, the diameter of the annular beam of light will be dependent upon the distance from the point of projection to point of capture by a surface, e.g., a tissue site, e.g., an interstitial cavity or lumen. Typically, when the purpose of the radiant energy projection is to form a transmural cardiac lesion, e.g., around a pulmonary vein, the diameter of the annular beam will be between about 10 mm and about 33 mm, preferably greater than 10 mm, greater than 15 mm, greater than 20 mm, and most preferably, greater than or equal to 23 mm. Typically, angle of projected annular light is between about 20° and about 60°, preferably between about 45° and about 55°, most preferably in some applications about 50° (total subtended angle 100°).

Preferred energy sources for use with the percutaneous ablation instruments of the present invention include laser light in the range between about 200 nanometers and 2.5 micrometers. In particular, wavelengths that correspond to, or are near, water absorption peaks are often preferred. Such wavelengths include those between about 805 nm and about 1060 nm, preferably between about 900 nm and 1000 nm, most preferably, between about 915 nm and 980 nm. In a preferred embodiment, wavelengths around 915 nm or around 980 nm are used during endocardial procedures. Suitable lasers include excimer lasers, gas lasers, solid state lasers and laser diodes. One preferred AlGaAs diode array, manufactured by Spectra Physics, Tucson, Ariz., produces a wavelength of 980 nm.

Referring back to FIG. 24, waveguide 144 can be coupled to optical fiber 142 by various methods known in the art. These methods include for example, gluing, or fusing with a torch or carbon dioxide laser. In one embodiment, waveguide 144, optical fiber 142 and, optionally, a gradient index lens (GRIN) 146 are in communication and are held in position by heat shrinking a polymeric jacket material 149, such as polyethylene teraphthalate (PET) about the optical apparatus 140.

The optical waveguides, as described in above, can be made from materials known in the art such as quartz, fused silica or polymers such as acrylics. Suitable examples of acrylics include acrylates, polyacrylic acid (PAA) and esters, methacrylates, and polymethacrylic acid (PMA) and esters. Representative examples of polyacrylic esters include polymethylacrylate (PMA), polyethylacrylate and polypropylacrylate. Representative examples of polymethacrylic esters include polymethylmethacrylate (PMMA), polyethylmethacrylate and polypropylmethacrylate. In one preferred embodiment, the waveguide 44 is formed of quartz and fused to the end face of fiber 42.

Internal shaping of the waveguide can be accomplished by removing a portion of material from a unitary body, e.g., a cylinder or rod. Methods known in the art can be utilized to modify waveguide to have tapered inner walls, e.g., by grinding, milling, ablating, etc. In one approach, a hollow polymeric cylinder, e.g., a tube, is heated so that the proximal end collapses and fuses together, forming an integral proximal portion which tapers to the distal end of the waveguide. In another approach, the conical surface 45 can be formed in a solid quartz cylinder or rod by drilling with a tapered bore.

Figure 25:
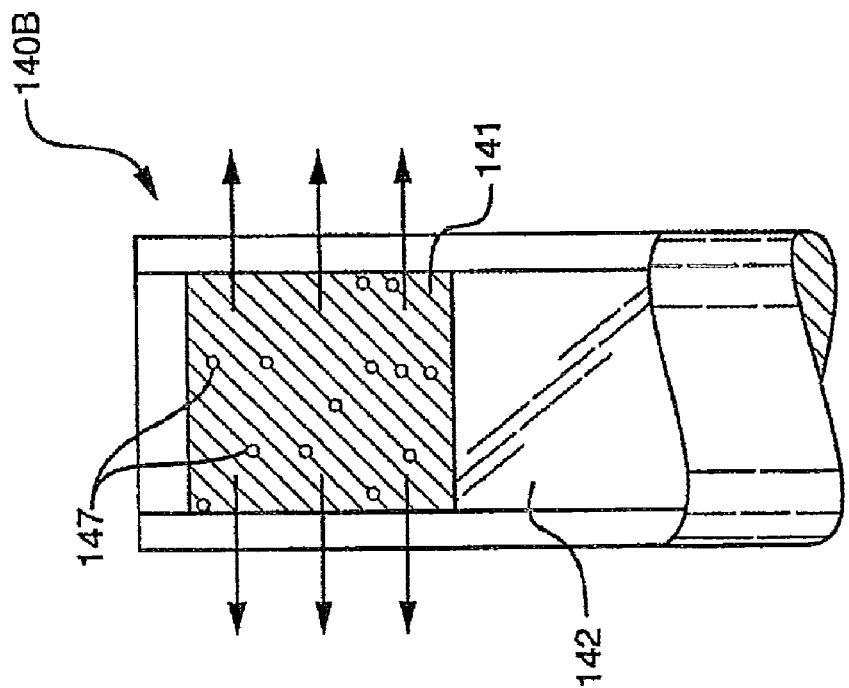
FIG. 25 is a schematic illustration of another embodiment of a radiant light energy emitter according to the invention.

A variety of other energy emitters can be used with the present invention, such as those discussed below. FIG. 25 is a schematic illustration of another embodiment of a radiant energy emitter 140B according to the invention in which optical fiber 142 is coupled to a light diffuser 141 having light scattering particles 147 to produce a sidewise cylindrical exposure pattern of ablative radiation. This embodiment can be useful, for example, in creating a lesion within a pulmonary vein. With reference again to FIG. 21, it should be clear that the radiant energy emitter of the design shown in FIG. 25 can be advanced to the front of the projection balloon to permit diffuse exposure of a pulmonary vein ostium if a lesion is desired in that location. For further details on the construction of light diffusing elements, see U.S. Pat. No. 5,908,415 issued to Sinofsky on Jun. 1, 1999, herein incorporated by reference.

Figure 26:
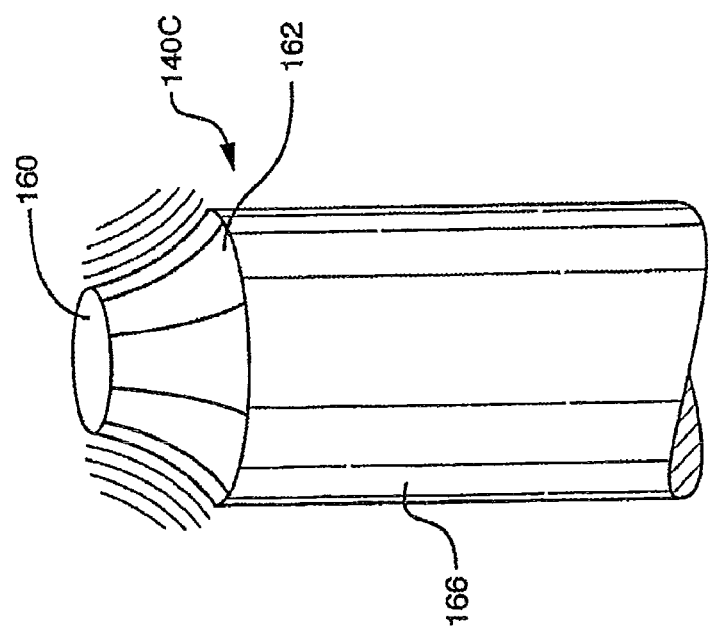
FIG. 26 is a schematic illustration of an alternative embodiment of a radiant energy emitter according to the invention employing ultrasound energy.

FIG. 26 illustrates an alternative embodiment of a radiant energy emitter 140C in which an ultrasound transducer 160 includes individual shaped transducer elements (and/or lenses or reflectors) 162 which direct (project) the ultrasound energy into a cone of energy that can likewise form an annular exposure pattern upon impingement with a target surface. The emitter 140C is supported by a sheath 166 or similar elongate body, that can, for example, enclose electrical leads, thereby permitting the clinician to advance the emitter through an inner lumen of the instrument to a desired position for ultrasound emission.

Figure 27:
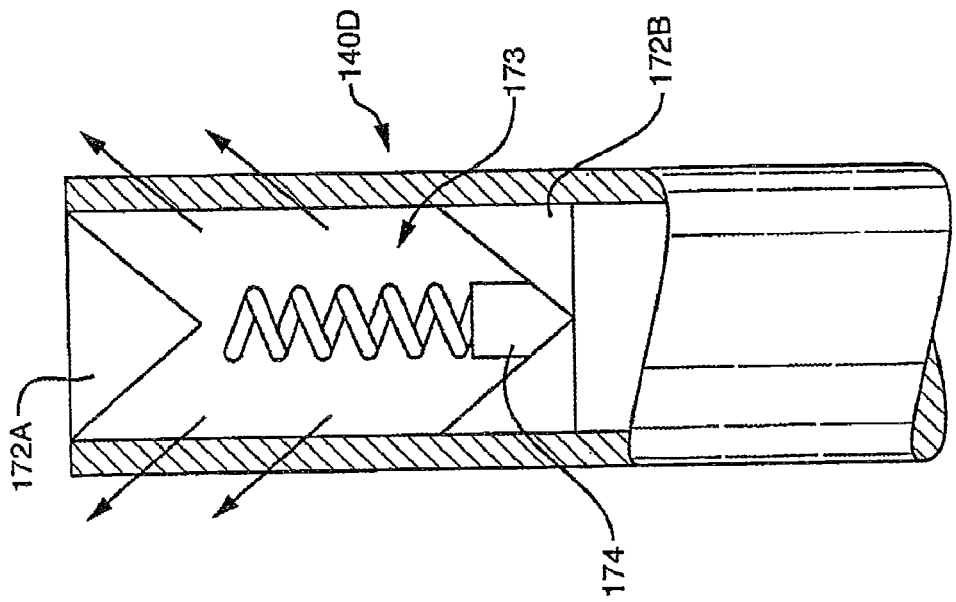
FIG. 27 is a schematic illustration of an alternative embodiment of a radiant light energy emitter according to the invention employing microwave or ionizing radiation.

Yet another embodiment of a radiant energy emitter 140D is illustrated in FIG. 27 where microwave energy is similarly focused into an annular exposure beam. As shown in FIG. 27, the radiant energy emitter 140D can include a coaxial transmission line 174 (or similar electrical signal leads) and a helical coil antenna 173. Radiation reflectors 172A and 172B cooperated to shield and direct the radiation into a cone. In other embodiments, a radioisotope or other source of ionizing radiation can be used in lieu of the microwave antenna 173, again with appropriate radiation shielding elements 172A and 172B to project a beam of ionizing radiation.

Figure 29:
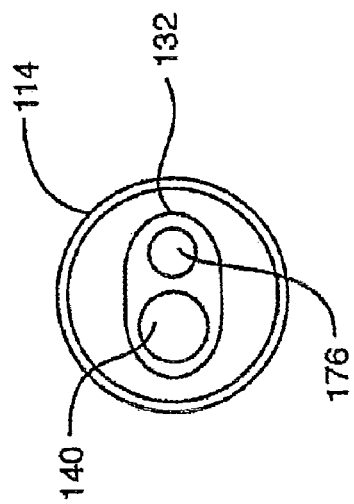
FIG. 29 is an end view, schematic illustration of the endoscope and ablator assembly shown in FIG. 28.
Figure 28:
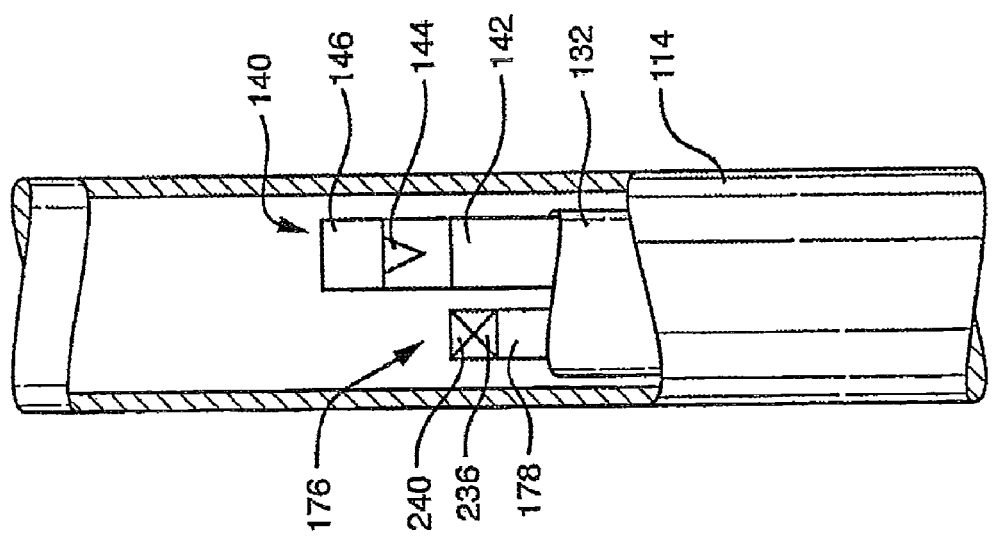
FIG. 28 is a schematic cross-sectional illustration of one embodiment of endoscope and ablator assembly according to the invention.
Figure 30:
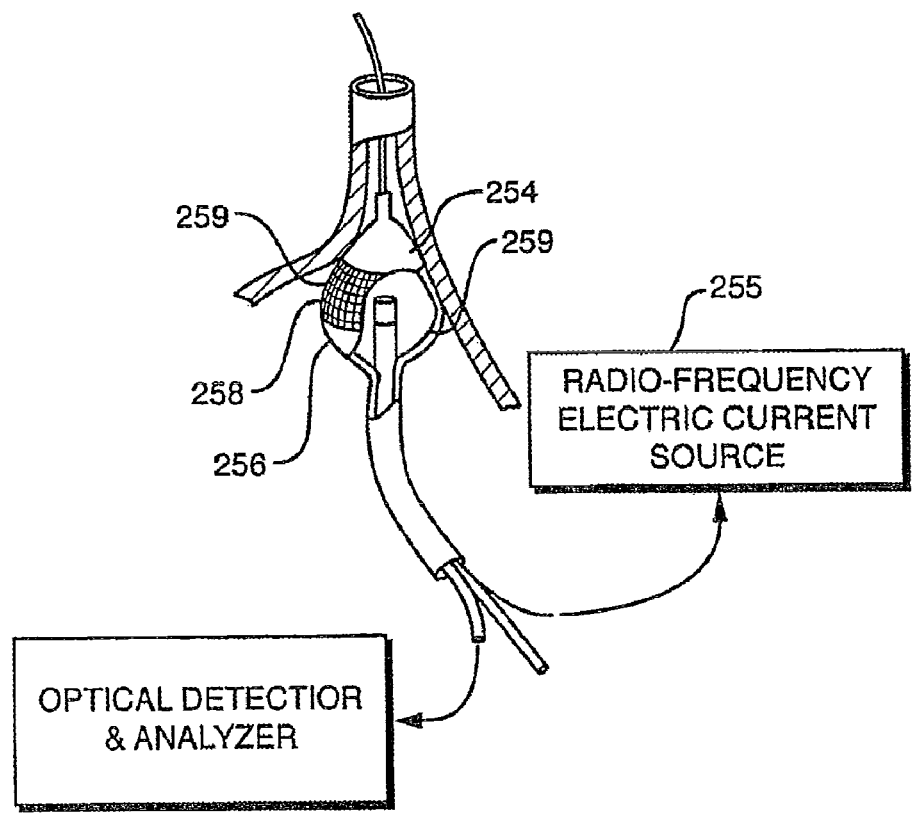
FIG. 30 is a schematic view of a contact heating ablation device employing the endoscope-guiding apparatus of the present invention.

FIGS. 28 and 29 illustrate one embodiment of a sensor incorporated into a radiant emitter assembly (such as those discussed above). As shown the assembly includes an assembly body 132 that encases an endoscope/ablator assembly and facilitates slidable positioning within an inner lumen of catheter body 114. The assembly further includes an energy emitter 140 (e.g., like those described above) as well as a reference sensor 176. In use, if the ablative element 140 of the invention is properly positioned within the heart, the ablative element 140 can act as an illumination light source such that light transmitted via such ablation element 140 will strike the target region, be reflected back, and detected by the reflectance sensor 176. While FIGS. 28 and 29 illustrate one ablative element 140 and one reflectance sensor 176, it should be clear that the invention can be practiced with various numbers of illuminating and/or sensing elements, e.g., two ablative elements and two reflectance sensors, as well as with or without use of the energy emitter as an element in the contact sensing module. The emitter and the endoscope can each move independently, if desired. Moreover, ultrasound emitters and detectors can also be used in the same manner in lieu of the light reflecting mechanisms to determine contact. In any event, the output signals of the sensors can be electronically processed and incorporated into a display.

The devices of the present invention can further include illumination elements that are capable of diffusing light to a large contact area of tissue by employing a scattering medium at the distal end of the illumination fiber. Any diffusing material can be used that allows high intensity light to be uniformly diffused over a large area (preferably over an area greater than 40 mm in diameter), such as, a matrix of titanium dioxide particles suspended in cured silicone.

Referring back to FIG. 28, endoscope 176, can include an optical fiber bundle 178 for transmitting the captured image back to a detector and display, as well as a lenses 236 and 240 which provide an enhanced field of view. Such field enhancing elements preferably increase the field of view to greater than 50°, more preferably to about 70° or higher. Typically, commercially available endoscopes have a field of view of about 50° or less in air. However, when immersed in water or similar fluids, the field of view of the endoscope is further reduced due to the refractive index difference between water and air. As explained in more detail below, a greater field of view is very important to endoscopic guidance.

One skilled in the art will appreciate that the endoscopes of FIGS. 28 and 29 provide the ability to position the percutaneous ablation instruments of the present invention at a treatment site such that proper location of the energy emitter vis-à-vis the target tissue (as well a satisfactory degree of contact between the projection balloon and the tissue) is achieved.

The endoscopes of the present invention can also be used in conjunction with other optical reflectance measurements of light scattered or absorbed by blood, body fluids and tissue. For example, white light projected by an illumination source toward tissue has several components including red and green light. Red light has a wavelength range of about 600 to about 700 nanometers (nm) and green light has a wavelength range of about 500 to about 600 nm. When the projected light encounters blood or body fluids, most if not all green light is absorbed and hence very little green or blue light will be reflected back toward the optical assembly which includes a reflected light collector. As the apparatus is positioned such that blood and body fluids are removed from the treatment field cleared by an inflated balloon member, the reflectance of green and blue light increases as biological tissue tends to reflect more green light. As a consequence, the amount of reflected green or blue light determines whether there is blood between the apparatus and the tissue or not.

Thus, the endoscopic displays of the present invention can incorporate filters (or generate "false-color" images) that emphasize the presence or absence of blood in the field. For example, when the inflated balloon member contacts the heart tissue (or is close enough that the balloon and ablative fluid released by the instrument form a clear transmission pathway), more green light will be reflected back into the optical assembly and the collector. The ratio of two or more different wavelengths can be used to enhance the image. Accordingly, a color-enhanced endoscope permit visualization of the instrument and/or the target site, as well as a determination of whether blood precludes the formation of a continuous lesion, e.g., circumferential lesion around the ostium of a pulmonary vein.

Alternatively, spectrographic measurements can be taken in tandem with endoscopic imaging, Thus, reflected light can be transmitted back through a collector, such as an optical fiber to a spectrophotometer. The spectrophotometer (such as spectrophotometer model S-2000 from Ocean Optics Spectrometer, Dunedin, Fla.) produces a spectrum for each reflected pulse of reflected light. Commercially available software (LabView Software, Austin, Tex.) can isolate values for specific colors and perform ratio analyses.

Once the operator is satisfied with the positioning of the instrument, radiant energy can then be projected to the target tissue region. If the radiant energy is electromagnetic radiation, e.g., laser radiation, it can be emitted onto the tissue site via a separate optical fiber or, alternatively, through the same optical fiber used to transmitting the white, green or red light. The laser light can be pulsed intermittently in synchronous fashion with the positioning/reflecting light to ensure that the pathway remains clear throughout the procedure.

It should be clear that the imaging and contact sensing aspects of the present invention are not limited to radiant energy ablation devices but can also be useful in placement of contact heating or cooling ablation instruments as well. For example, in FIG. 30, a contact-heating device 254 having an expandable element 256 and a contact heating element 258 is shown disposed in a pulmonary vein. The contact heating element 258 can be a line or grid of electrically conductive material printed on the surface of the expandable element 256. In one embodiment, the expandable element 256 can be substantially opaque to certain wavelengths (e.g., visible light) except for a transparent band 259, on which the contact heating element is situated. The heating wires should also be sufficiently transparent (or cover a substantially small area of the band) so as to not interfere with reflection signal collection. The device 254 can further include a sensor, e.g., an endoscope, disposed within a central lumen of the device having an illuminating fiber and a plurality of collecting fibers.

Figure 31:
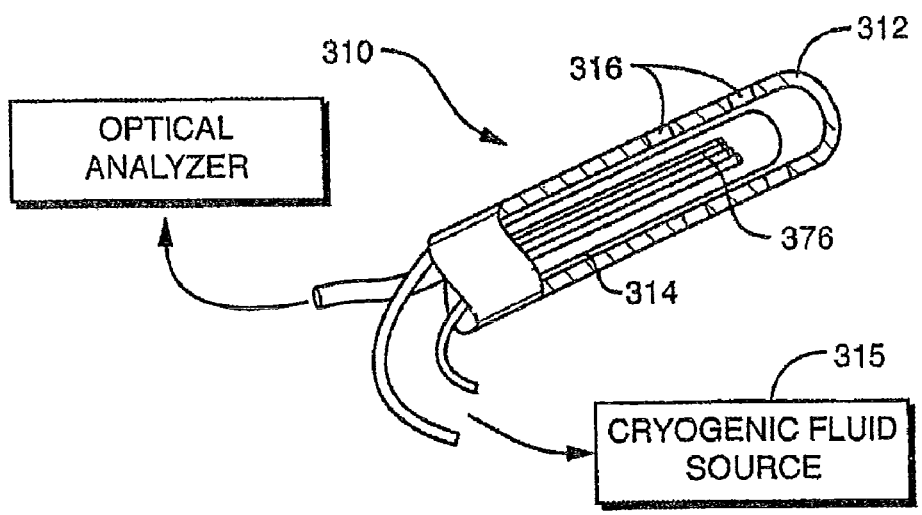
FIG. 31 is a schematic view of a cryogenic ablation device employing the endoscope-guiding apparatus of the present invention.

In FIG. 31, another embodiment of a reflectance sensing or endoscope-guided catheter is shown in the form of a cryogenic ablation catheter 310 having a catheter body 312 and internal conduits 314 for circulation of a cryogenic fluid from a cryogenic fluid source 315. The catheter body 312 can include an expandable portion, e.g., a balloon structure, and further includes conductive regions 316 where the cold temperature can be applied to tissue. The endoscope 376 of the present invention can be disposed in proximity to the conductive regions, as shown and used to determine whether tissue contact has been made.

Figure 32:
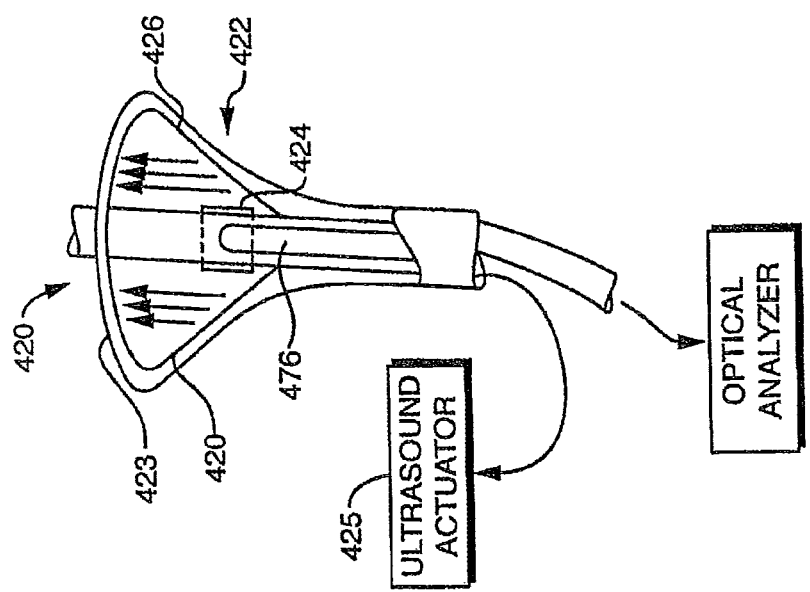
FIG. 32 is a schematic view of an ultrasound heating ablation device employing the contacting sensing apparatus of the present invention.

FIG. 32 illustrates yet another application for the contact sensors. As shown, the contact sensor can be used in connection with an ultrasound, contact-heating balloon catheter 420 having a balloon 422 (similar to those discussed above) for contacting a pulmonary vein ostium and having an optional band 423 for applying heat to tissue. The ultrasound ablation instrument 420 further includes transducers 424 driven by actuator 425 to heat a desired region of tissue. The instrument 420 can also include reflectors 426 to project the ultrasound energy through the balloon into an annular focus in the target tissue (or at the surface of the balloon). Again, the reflectance or endoscopic sensors 476 of the present invention can be disposed within the balloon or catheter body, as shown, and used to determine whether tissue contact has been made.

Figure 33:
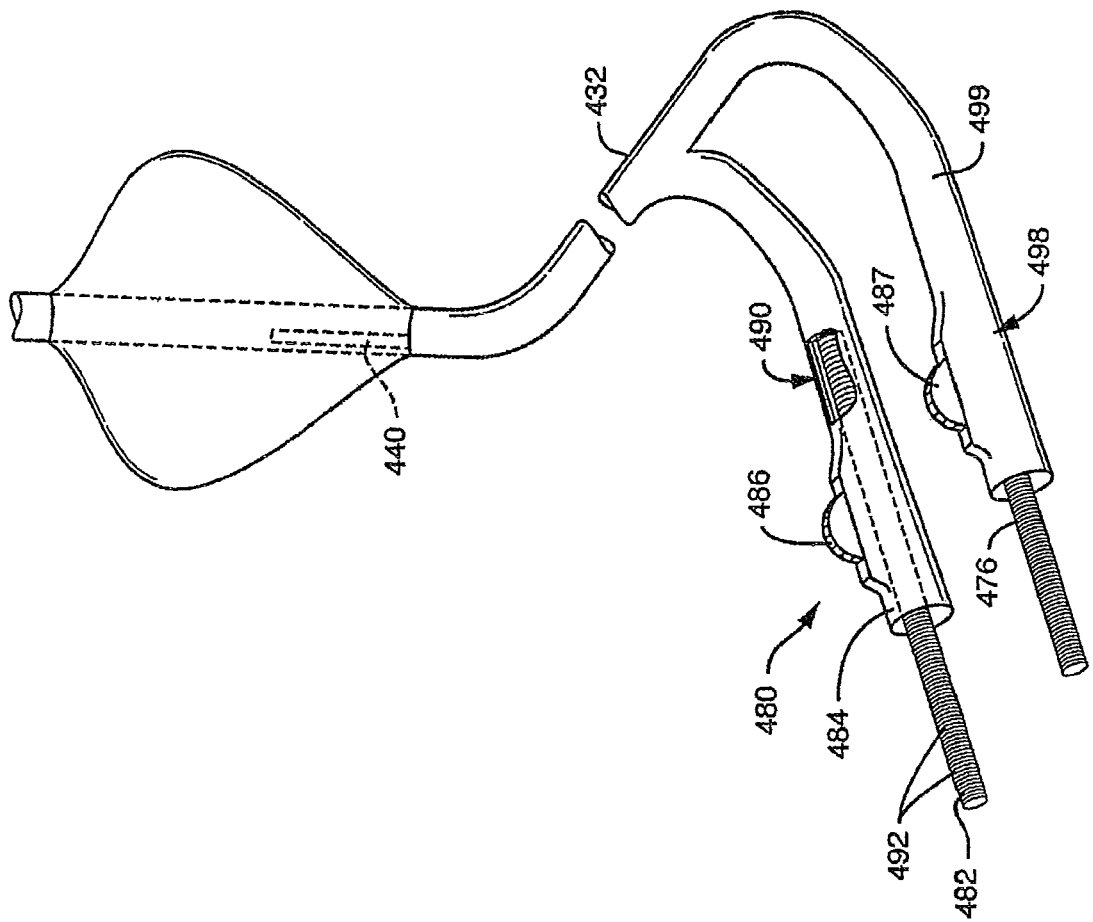
FIG. 33 is a schematic illustration of a translation system for independently positioning the endoscope and ablation components of an endoscope/ablator assembly during a procedure.

In FIG. 33, an assembly 432 is shown having a translatory mechanism 480 for controlled movement of a radiant energy emitter 440. The translatory mechanism 480 is similar to that discussed above, that is the exemplary translatory mechanism 480 is incorporated into a handle 484 in the proximal region of the instrument, where the elongate body 482 of the radiant energy emitter 440 engages a thumb wheel 486 to control advancement and retraction of the emitter. Moreover, various alternative mechanisms of manual or automated nature can be substituted for the illustrated thumb wheel 486 to position the emitter at a desired location relative to the target tissue region.

The assembly 432 of FIG. 33 can also include additional features. For example, the elongate body 482 that supports the ablation instrument can further include position indicia 492 on its surface to assist the clinician in placement of the ablation element within the instrument. The handle can further include a window 490 whereby the user can read the indicia (e.g., gradation markers) to gauge how far the emitter has been advanced into the instrument.

Moreover, the assembly 432 can include an endoscope translatory mechanism 498 for controlled movement of the reflectance sensor or endoscope 476 within the instruments of the present invention. The exemplary positioner 498 can be incorporated into a handle 499 in the proximal region of the instrument, where the elongate body of the sensor 476 engages a thumb wheel 497 to control advancement and retraction of the emitter.

In use, the separate branches for both the emitter 440 as well as the endoscope 476 allow the endoscope to be extracted prior to the entry/advancement of the emitter 440 into the target tissue site. One skilled in the art will appreciate that this can prevent the endoscope 476 from being damaged by the energy from the emitter 440.

One skilled in the art will also appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A cardiac ablation instrument assembly comprising:
   a deflectable first catheter adapted for disposition within a heart having at least one lumen therein extending from a proximal end to a distal end, the catheter having a deflectable end section formed of a plurality of flexible polymeric segments, at least one polymeric segment having a different stiffness as compared to another polymeric segment of the deflectable end section thereby allowing the deflectable end section to form a compound curve upon deployment and deflection within the heart;
   an elongate second catheter for disposition within a heart;

an expandable balloon member having a wall coupled to the elongate second catheter and sized for positioning proximate to a pulmonary vein;
a radio-frequency (RF) ablation element within the balloon member for creating at least one lesion proximate the pulmonary vein by being configured to convey a sufficient amount of energy through the balloon wall to create the at least one lesion; and
wherein the lumen is sized and configured to allow passage of the elongate second catheter, the balloon member, and the ablation element contained within the balloon member.

2. The assembly of claim 1, wherein the stiffness of a distal section of the first catheter decreases in a distal direction along at least a portion of the distal section.

3. The assembly of claim 1, wherein the polymeric segments comprise Pbax polymer.

4. The assembly of claim 1, wherein the elongate second catheter comprises at least one braided wire reinforcement layer.

5. The assembly of claim 4, wherein the elongate second catheter comprises at least one braided wire cladding surrounding at least a portion of the second catheter's length.

6. The assembly of claim 4, wherein the reinforcement layer is continuous.

7. The assembly of claim 4, wherein the reinforcement layer is discontinuous.

8. The assembly of claim 4, wherein the reinforcement layer is varied to provide segments of different stiffness.

9. The assembly of claim 1, further comprising an actuator that effects deflection of the deflectable end section.

10. The assembly of claim 9, wherein the actuator further comprises a lock to fix the deflectable end section in a particular curve within its range of movement.

11. The assembly of claim 10, wherein the actuator further comprises a pull wire mechanically linking the deflectable end section to a proximal handle portion.

12. The assembly of claim 1, wherein the stiffness of the plurality of segments varies progressively over at least a portion of the deflectable end section.

13. The assembly of claim 1, wherein the deflectable end section includes at least one irrigation port.

14. The assembly of claim 1, wherein the deflectable end section includes at least one radiopaque band.

15. The assembly of claim 1, wherein the proximal end of the deflectable first catheter comprises a handle.

16. The assembly of claim 15, wherein the handle comprises at least one hemostasis valve.

17. The assembly of claim 1, wherein the deflectable end section further comprises a distal tip that is bent out of a plane of deflection.

18. The assembly of claim 1, wherein the deflectable end section has a distal taper.

19. The assembly of claim 1, wherein the RF ablation element comprises one or more conductive region(s).

20. A cardiac energy delivery instrument assembly comprising:
a deflectable first catheter adapted for disposition within a heart having at least one lumen therein extending from a proximal end to a distal end, the catheter having a deflectable end section formed of a plurality of flexible polymeric segments, at least one polymeric segment having a different stiffness as compared to another polymeric segment of the deflectable end section thereby allowing the deflectable end section to form a compound curve upon deployment and deflection within the heart;
an elongate second catheter for disposition within a heart;
an expandable balloon member having a wall coupled to the elongate second catheter and sized for positioning proximate to a pulmonary vein;
a radio-frequency (RF) energy delivery element within the balloon member for conveying energy through the balloon wall; and
wherein the lumen is sized and configured to allow passage of the elongate second catheter, the balloon member, and the energy delivery element contained within the balloon member.

21. The assembly of claim 20, further comprising an actuator that effects deflection of the deflectable end section, the actuator comprising a pull wire mechanically linking the deflectable end section to a proximal handle portion and a lock to fix the deflectable end section in a particular curve within its range of movement.

22. The assembly of claim 21, wherein the stiffness of a distal section of the first catheter decreases in a distal direction along at least a portion of the distal section.

23. The assembly of claim 21, wherein the elongate second catheter comprises at least one braided wire reinforcement layer.

24. The assembly of claim 21, wherein the reinforcement layer is varied to provide segments of different stiffness.

25. The assembly of claim 23, wherein the RF energy delivery element comprises one or more conductive region(s).

\* \* \* \* \*